(12) United States Patent
Deluca et al.

(10) Patent No.: US 11,697,635 B2
(45) Date of Patent: Jul. 11, 2023

(54) PROCEDURE FOR CRYSTALLIZATION OF (22E)-(24R)-2-METHYLENE-22-DEHYDRO-1α,24-25-TRIHYDROXY-19-NOR-VITAMIN $D_3$

(71) Applicant: Wisconsin Alumni Research Foundation, Madison, WI (US)

(72) Inventors: Hector F. Deluca, Deerfield, WI (US); Margaret Clagett-Dame, Deerfield, WI (US); Lori Plum, Arena, WI (US); Agnieszka Flores, Sun Prairie, WI (US); James Thoden, Madison, WI (US); Hazel Holden, Fitchburg, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 16/755,212

(22) PCT Filed: Oct. 16, 2018

(86) PCT No.: PCT/US2018/056057
§ 371 (c)(1),
(2) Date: Apr. 10, 2020

(87) PCT Pub. No.: WO2019/079279
PCT Pub. Date: Apr. 25, 2019

(65) Prior Publication Data
US 2020/0262773 A1 Aug. 20, 2020

Related U.S. Application Data

(60) Provisional application No. 62/573,387, filed on Oct. 17, 2017.

(51) Int. Cl.
| | | |
|---|---|---|
| *C07C 401/00* | (2006.01) | |
| *A61P 3/02* | (2006.01) | |
| *A61P 3/04* | (2006.01) | |
| *A61K 31/593* | (2006.01) | |
| *A61P 35/00* | (2006.01) | |
| *C07C 35/21* | (2006.01) | |
| *C07C 29/78* | (2006.01) | |

(52) U.S. Cl.
CPC .......... *C07C 401/00* (2013.01); *A61K 31/593* (2013.01); *A61P 3/02* (2018.01); *A61P 3/04* (2018.01); *A61P 35/00* (2018.01); *C07C 29/78* (2013.01); *C07C 35/21* (2013.01); *C07B 2200/13* (2013.01); *C07C 2601/14* (2017.05); *C07C 2602/24* (2017.05)

(58) Field of Classification Search
None
See application file for complete search history.

(56) References Cited

U.S. PATENT DOCUMENTS

| | | | |
|---|---|---|---|
| 3,168,535 A | * 2/1965 | Martin | C07C 401/00 552/653 |
| 8,404,874 B2 | 3/2013 | Deluca | |
| 8,420,839 B1 | * 4/2013 | DeLuca | C07C 401/00 552/653 |
| 8,519,169 B2 | 8/2013 | DeLuca | |
| 8,884,039 B2 | 11/2014 | DeLuca | |
| 8,940,916 B2 | 1/2015 | DeLuca | |
| 9,040,729 B2 | 5/2015 | Lutz | |
| 9,212,137 B2 | 12/2015 | DeLuca | |
| 9,416,102 B2 | 8/2016 | DeLuca | |
| 2013/0324752 A1 | * 12/2013 | DeLuca | C07C 401/00 552/653 |
| 2014/0206655 A1 | 7/2014 | DeLuca | |

FOREIGN PATENT DOCUMENTS

| | | | | |
|---|---|---|---|---|
| CN | 103819379 A | * | 5/2014 | |
| WO | 2003088977 A1 | | 10/2003 | |
| WO | WO-2011002756 A2 | * | 1/2011 | ........... A23K 20/174 |
| WO | 2014116386 A1 | | 7/2014 | |

OTHER PUBLICATIONS

Mullin ("Crystallization and Precipitation", 2005, pp. 1-51).*
Andrews, D. R., et al. "A direct, regio-and stereoselective 1. alpha.-hydroxylation of (5E)-calciferol derivatives." The Journal of Organic Chemistry 51.9 (1986): 1635-1637.
Caira, M. R. "Crystalline polymorphism of organic compounds." Design of Organic Solids. Springer, Berlin, Heidelberg, 1998. 163-208.
Calverley, M. J. "Synthesis of MC 903, a biologically active vitamin D metabolite analogue." Tetrahedron 43.20 (1987): 4609-4619.
Choudhry, S. C., et al. "Synthesis of a biologically active vitamin D2 metabolite." The Journal of Organic Chemistry 58.6 (1993): 1496-1500.
International Searching Authority. International Search Report and Written Opinion for application PCT/US2018/056057. dated Feb. 4, 2019.
Nerinckx, W., et al. "An improved synthesis of 1a-hydroxy vitamin D3." Tetrahedron 47.45 (1991): 9419-9430.
Paaren, H.E., et al. "Direct C (1) hydroxylation of vitamin D3 and related compounds." The Journal of Organic Chemistry 45.16 (1980): 3253-3258.
Paaren, H.E., et al. "Direct C-1 hydroxylation of vitamin D compounds: convenient preparation of 1alpha-hydroxyvitamin D3, 1 alpha, 25-dihydroxyvitamin D3, and 1 alpha-hydroxy vitamin D2." Proceedings of the National Academy of Sciences 75.5 (1978): 2080-2081.

(Continued)

*Primary Examiner* — Rosalynd A Keys
(74) *Attorney, Agent, or Firm* — Quarles & Brady LLP

(57) ABSTRACT

Disclosed are methods of purifying the compound (22E)-(24R)-2-methylene-22-dehydro-1α,24,25-trihydroxy-19-nor-vitamin $D_3$ to obtain the compound in crystalline form. The methods typically include the steps of dissolving (22E)-(24R)-2-methylene-22-dehydro-1α,24,25-trihydroxy-19-nor-vitamin $D_3$ in a solvent comprising ethyl acetate and hexane to form a solution, allowing crystals of (22E)-(24R)-2-methylene-22-dehydro-1α,24,25-trihydroxy-19-nor-vitamin $D_3$ to form and precipitate from the solution, and recovering the crystals of (22E)-(24R)-2-methylene-22-dehydro-1α,24,25-trihydroxy-19-nor-vitamin $D_3$ from the solution.

17 Claims, 4 Drawing Sheets

(56) References Cited

OTHER PUBLICATIONS

Vanmaele, L. J., et al. "A stereocontrolled partial synthesis of 1a-hydroxy vitamin D3." Tetrahedron Letters 23.9 (1982): 995-998.
Vanmaele, L. J., et al. "An efficient synthesis of 1a, 25-dihydroxy vitamin D3." Tetrahedron (Oxford. Print) 41.1 (1985): 141-144.
Vanmaele, L. J., et al. "Ia-hydroxy previtamin D3, and its selective formation from 1-keto previtamin D3." Tetrahedron 40.7 (1984): 1179-1182.

* cited by examiner

PROCEDURE FOR CRYSTALLIZATION OF (22E)-(24R)-2-METHYLENE-22-DEHYDRO-1α, 24-25-TRIHYDROXY-19-NOR-VITAMIN $D_3$

CROSS-REFERENCE TO RELATED PATENT APPLICATIONS

The present application is the U.S. National Stage of International Application PCT/US2018/056057, filed on Oct. 16, 2018, which claims the benefit of priority under 35 U.S.C. § 119(e) to U.S. Provisional Application No. 62/573, 387, filed on Oct. 17, 2017, the contents of which are incorporated herein by reference in their entireties.

BACKGROUND

The field of the invention relates to vitamin D compounds, and more particularly to (22E)-2-methylene-22-dehydro-1α, 24,25-trihydroxy-19-nor-vitamin $D_3$ analogs and their pharmaceutical uses. In particular, the field of the invention relates to procedures for crystallizing vitamin D compounds such as (22E)-(24R)-2-methylene-22-dehydro-1α,24,25-trihydroxy-19-nor-vitamin $D_3$.

Purification of organic compounds, especially those designated for pharmaceutical use, is of considerable importance for chemists synthesizing such compounds. Preparation of the compound usually requires many synthetic steps and, therefore, the final product can be contaminated not only with side-products derived from the last synthetic step of the procedure but also with compounds that were formed in previous steps. Even chromatographic purification, which is a very efficient but relatively time-consuming process, does not usually provide compounds which are sufficiently pure to be used as drugs.

Depending on the method used to synthesize 1α-hydroxyvitamin D compounds, different minor undesirable compounds can accompany the final product. Thus, for example, if direct C-1 hydroxylation of the 5,6-trans geometric isomer of vitamin D is performed, followed by $SeO_2$/NMO oxidation and photochemical irradiation, (see Andrews et al., *J. Org. Chem.* 51, 1635 (1986); Calverley et al., *Tetrahedron* 43, 4609 (1987); Choudry et al., *J. Org. Chem.* 58, 1496 (1993)), the final 1α-hydroxyvitamin D product can be contaminated with 1β-hydroxy-as well as 5,6-trans isomers. If the method consists of C-1 allylic oxidation of the 4-phenyl-1,2,4-triazoline-3,5-dione adduct of the pre-vitamin D compound, followed by cycloreversion of the modified adduct under basic conditions, (see Nevinckx et al., *Tetrahedron* 47, 9419 (1991); Vanmaele et al., *Tetrahedron* 41, 141 (1985) and 40, 1179 (1994); Vanmaele et al., *Tetrahedron Lett.* 23. 995 (1982)), one can expect that the desired 1α-hydroxyvitamin can be contaminated with the pre-vitamin 5(10), 6,8-triene and 1β-hydroxy isomer. One of the most useful C-1 hydroxylation methods, of very broad scope and numerous applications, is the experimentally simple procedure elaborated by Paaren et al., *J. Org. Chem.* 45, 3253 (1980); and *Proc. Natl. Acad. Sci U.S.A.* 75, 2080 (1978). This method consists of allylic oxidation of 3,5-cyclovitamin D derivatives, readily obtained from the buffered solvolysis of vitamin D tosylates, with $SeO_2$/t-BuOOH and subsequent acid-catalyzed cycloreversion to the desired 1α-hydroxy compounds. Taking into account this synthetic path it is reasonable to assume that the final product can be contaminated with the 1α-hydroxy epimer, the 5,6-trans isomer and the pre-vitamin D form. 1α-hydroxyvitamin $D_4$ is another undesirable contaminant found in 1α-hydroxyvitamin D compounds synthesized from vitamin $D_2$ or from ergosterol. 1α-hydroxyvitamin $D_4$ results from C-1 oxidation of vitamin $D_4$, which in turn is derived from contamination of the commercial ergosterol material. Typically, the final product may contain up to about 1.5% by weight 1α-hydroxyvitamin $D_4$. Thus, a purification technique that would eliminate or substantially reduce the amount of 1α-hydroxyvitamin $D_4$ in the final product to less than about 0.1-0.2% would be highly desirable.

The vitamin D conjugated triene system is not only heat- and light-sensitive but it is also prone to oxidation, leading to the complex mixture of very polar compounds. Oxidation usually happens when a vitamin D compound has been stored for a prolonged time. Other types of processes that can lead to a partial decomposition of vitamin D compounds consist of some water-elimination reactions. The driving force for these reactions is the allylic (1α-) and homoallylic (3β-) position of the hydroxy groups. The presence of such above-mentioned oxidation and elimination products can be easily detected by thin-layer chromatography.

Usually, all 1α-hydroxylatation procedures require at least one chromatographic purification. However, even chromatographically purified 1α-hydroxyvitamin D compounds, although showing consistent spectroscopic data that suggests homogeneity, do not meet the purity criteria required for therapeutic agents that can be orally, parenterally or transdermally administered.

Therefore, improved purification procedures for vitamin D compounds are desirable such as crystallization procedures. Here, the present inventors disclose procedures for crystallizing (22E)-(24R)-2-methylene-22-dehydro-1α,24, 25-trihydroxy-19-nor-vitamin $D_3$.

SUMMARY

Disclosed herein are procedures for purifying (22E)-(24R)-2-methylene-22-dehydro-1α,24,25-trihydroxy-19-nor-vitamin $D_3$, otherwise referred to as "WT-51" by means of crystallization to obtain WT-51 in crystalline form.

The disclosed crystallization procedures utilize a solvent to dissolve WT-51. The solvent plays an important role in the crystallization procedure, and is typically an individual liquid substance or a suitable mixture of different liquids. For crystallizing WT-51, the most appropriate solvent and/or solvent system is characterized by the following factors: (1) low toxicity; (2) low boiling point (e.g. less than about 100, 90, or 80° C.); (3) significant dependence of solubility properties with regard to temperature (condition necessary for providing satisfactory crystallization yield); and (4) relatively low cost.

Interestingly, a mixture of ethyl acetate and hexane was found to be a suitable solvent for the crystallization of WT-51. In particular, it was determined that a mixture of about 20% to about 30% ethyl acetate (v/v) with about 80% to about 70% hexane (v/v) was a suitable solvent for the crystallization of WT-51. In the disclosed method, WT-51 first was dissolved in ethyl acetate and hexane was added dropwise to reach a saturation point. After sitting at room temperature, crystals of WT-51 began to grow after about 1 hour. The ethyl acetate/hexane solvent mixture also was easy to remove by evaporation or other well-known methods. The precipitated crystals were sufficiently large to assure their recovery by filtration or other means, and thus were suitable for X-ray diffraction analysis.

Accordingly, the present invention provides a compound having the formula:

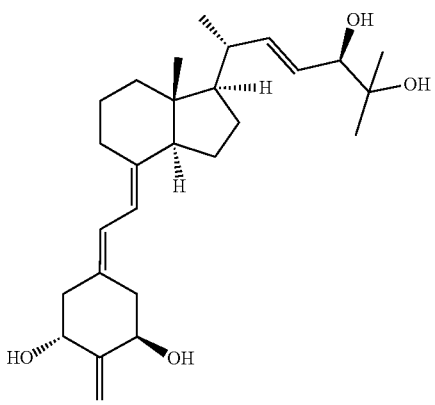 [SMILES: C=C1[C@H](O)CC(=C/C=C2\CCC[C@]3(C)[C@@H]([C@H](C)/C=C/[C@@H](O)C(C)(C)O)CC[C@@H]23)C[C@H]1O]

in crystalline form. More specifically, the compound may be referred to as (22E)-(24R)-2-methylene-22-dehydro-1α,24,25-trihydroxy-19-nor-vitamin $D_3$, or "WT-51" in crystalline form.

The crystalline forms of WT-51 may be formulated as a pharmaceutical composition comprising a crystalline form of WT-51 and a suitable carrier. The pharmaceutical compositions may be administered to a subject in need thereof for treating a variety of conditions that are treated and/or prevented by vitamin D compounds.

In some embodiments, the crystalline forms of WT-51 disclosed herein may be utilized in methods for treating and/or preventing skin diseases, disorders, and conditions in a subject in need thereof. These may include, but are not limited to psoriasis, acne, lack of adequate skin firmness, lack of adequate dermal hydration, and insufficient sebum secretion.

In further embodiments, the crystalline forms of WT-51 disclosed herein may be utilized in methods for treating and/or preventing cell proliferative diseases or disorders such as cancer in a subject in need thereof. These may include, but are not limited to leukemia, colon cancer, breast cancer, skin cancer, and prostate cancer.

In even further embodiments, the crystalline forms of WT-51 disclosed herein may be utilized in methods for treating and/or preventing autoimmune diseases and disorders in a subject in need thereof. These may include, but are not limited to multiple sclerosis, diabetes mellitus, lupus, host versus graft reaction, and rejection of transplants.

In even further embodiments, the crystalline forms of WT-51 disclosed herein may be utilized in methods for treating and/or preventing inflammatory diseases. These may include, but are not limited to rheumatoid arthritis, asthmas, and inflammatory bowel diseases. The crystalline forms of WT-51 may be utilized specifically in methods of treating or preventing inflammatory bowel diseases that include Crohn's disease and ulcerative colitis.

In even further embodiments, the crystalline forms of WT-51 disclosed herein may be utilized in methods for treating and/or preventing obesity, inhibiting adipocyte differentiation, inhibiting SCD-1 gene transcription, and/or reducing body fat.

DETAILED DESCRIPTION

Figure 1:
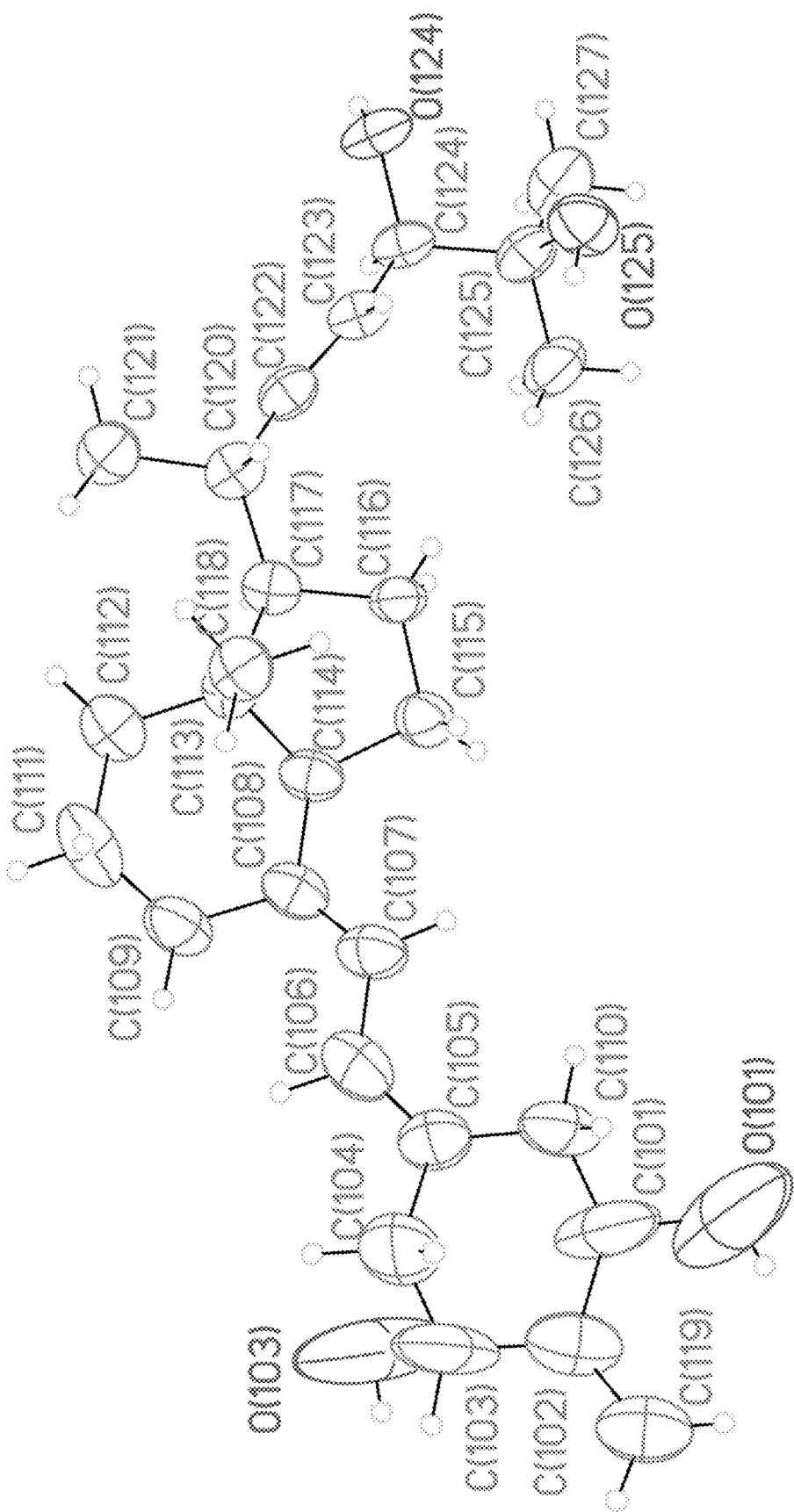
FIG. 1 is an illustration of one embodiment of a three dimensional molecular structure for WT-51 as defined by the atomic positional parameters discovered and set forth herein.

The disclosed subject matter further may be described utilizing terms as defined below.

Unless otherwise specified or indicated by context, the terms "a", "an", and "the" mean "one or more." For example, the phrases "a compound" and "an analog" should be interpreted to mean "one or more compounds" and "one or more analogs," respectively.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The transitional term "comprising" should be interpreted as being "open-ended" such that a claim utilizing the term "comprising" should be interpreted as requiring the recited components but being permitted to include other additional components. The transitional term "consisting essentially of" should be interpreted as being "partially closed" such that a claim utilizing the term "consisting essentially of" should be interpreted as requiring the recited components and permitting only other additional components that do not materially affect the basic and novel characteristics of the claimed subject matter. The transitional term "consisting" should be interpreted as being "closed" such that a claim utilizing the term "consisting" should be interpreted as requiring the recited components and permitting no other additional components.

As used herein, the terms "native hormone" and "1α,25 $(OH)_2D_3$," may be used interchangeably.

As used herein, the compound "WT-51" refers to (22E)-(24R)-2-methylene-22-dehydro-1α,24,25-trihydroxy-19-nor-vitamin $D_3$. Methods for synthesizing WT-51 are disclosed, for example, in U.S. Pat. No. 9,416,102, the content of which is incorporated herein by reference in its entirety.

As disclosed herein, the crystalline forms of WT-51 may be utilized to treat and/or prevent diseases or disorders in a subject in need thereof. The terms "subject," "patient," and "individual" may be used interchangeably herein.

A subject in need thereof may include any animal. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

A subject in need thereof may refer to subject having or at risk for acquiring a disease or disorders associated with vitamin D activity. For example, a subject in need thereof may include a subject having or at risk for acquiring bone diseases and disorders, which may include, metabolic bone diseases and disorders where an increase in bone mass is desirable such as osteoporosis (e.g., senile osteoporosis, postmenopausal osteoporosis, steroid-induced osteoporosis, and low bone-turnover osteoporosis), osteopenia, and osteomalacia. A subject in need thereof may also include a subject in need of an increase in bone strength.

A subject in need thereof may include a subject having or at risk for developing skin diseases, disorders, and conditions. These may include, but are not limited to psoriasis, acne, lack of adequate skin firmness, lack of adequate dermal hydration, and insufficient sebum secretion.

A subject in need thereof may include a subject having or at risk for developing cell proliferative diseases or disorders such as cancer. These may include, but are not limited to leukemia, colon cancer, breast cancer, skin cancer, and prostate cancer.

A subject in need thereof may include a subject having or at risk for developing autoimmune diseases and disorders. These may include, but are not limited to multiple sclerosis, diabetes mellitus, lupus, host versus graft reaction, and rejection of transplants.

A subject in need thereof may include a subject having or at risk for developing an inflammatory disease or disorder. These may include, but are not limited to rheumatoid arthritis, asthmas, and inflammatory bowel diseases. A subject in need thereof may include having or at risk for developing Crohn's disease and ulcerative colitis.

A subject in need thereof may include a subject having or at risk for developing obesity. A subject in need thereof may include a subject in need of or desirous of inhibiting adipocyte differentiation, inhibiting SCD-1 gene transcription, and/or reducing body fat.

A subject in need thereof may include a subject having or at risk for developing secondary hyperparathyroidism. In particular, a subject in need thereof may include a subject having or at risk for developing secondary hyperparathyroidism of renal osteodystrophy.

For prevention and/or treatment purposes, the crystalline forms of WT-51 may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The crystalline forms of WT-51 may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications.

A dose of from 0.01 μg to 1000 μg per day of the crystalline forms of WT-51, preferably from about 0.1 μg to about 500 μg per day, is appropriate for prevention and/or treatment purposes, such dose being adjusted according to the disease to be treated, its severity and the response of the subject as is well understood in the art. Because the compound exhibits specificity of action, each may be suitably administered alone, or together with graded doses of another active vitamin D compound (e.g., 1α-hydroxyvitamin $D_2$ or $D_3$, or 1α,25-dihydroxyvitamin $D_3$) in situations where different degrees of bone mineral mobilization and calcium transport stimulation is found to be advantageous.

Compositions for use in the above-mentioned treatments comprise an effective amount of crystalline forms of WT-51 as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually, or parenterally in dosages of from about 0.01 μg/day to about 1000 μg/day, and preferably from about 0.1 μg/day to about 500 μg/day.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient, for example, in the form of a crystalline powder or crystalline granules.

The formulations may conveniently be presented in dosage unit form and may be prepared by any of the methods well known in the art of pharmacy. By the term "dosage unit" is meant a unitary, i.e. a single dose which is capable of being administered to a subject as a physically and chemically stable unit dose comprising either the active ingredient as such or a mixture of it with solid or liquid pharmaceutical diluents or carriers.

EXAMPLES

The following Examples are illustrative and are not intended to limit the scope of the claimed subject matter.

Example 1—Preparation of (22E)-(24R)-2-methylene-22-dehydro-1α,24,25-trihydroxy-19-nor-vitamin $D_3$ (WT-51)

(22E)-(24R)-2-methylene-22-dehydro-1α,24,25-trihydroxy-19-nor-vitamin $D_3$ (WT-51) was synthesized as previously described. (See U.S. Pat. No. 9,416,102, the content of which is incorporated herein by reference in its entirety).

(22E)-Des-A,B-8β-benzoyloxy-24-oxo-25-[(triethylsilyl)oxy]-22-dehydrocholestan (3)

To a stirred solution of 2 (Scheme 1; 250 mg; 0.64 mmol) in tetrahydrofuran (1.5 ml) 1 M solution of lithium hexamethyldisilazide in tetrahydrofuran (700 μl; 0.70 mmol) was added dropwise. After 1 h a solution of $1^1$ (200 mg; 0.64 mmol) in tetrahydrofuran (1.5 ml) was added via cannula. The reaction mixture was stirred for 3 days. Then saturated aqueous solution of $NH_4Cl$ (2 ml), brine (2 ml) and water (5 ml) was added at 0° C. and the resulting mixture was extracted with methylene dichloride (3×50 ml). Organic phase was dried over anhydrous $Na_2SO_4$, concentrated under reduced pressure and the residue was purified by column chromatography (2-5% ethyl acetate/hexane) to give 200 mg (0.39 mmol; 61% yield) of 3. $[α]_D$=+94.3 (c 1.1, $CHCl_3$); $^1$H NMR (400 MHz, $CDCl_3$) δ 0.60 (6H, q, J=7.9 Hz), 0.95 (9H, t, J=7.9 Hz), 1.10 (3H, s), 1.12 (3H, d, J=6.6 Hz), 1.34 (6H, s), 2.04 (2H, m) 2.32 (1H, m), 5.42 (1H, br d, J=1.9 Hz), 6.71 (1H, d, J=15.4 Hz), 6.84 (1H, dd, J=15.4

Hz, J=8.6 Hz), 7.45 (2H, t, J=7.4 Hz), 7.56 (1H, t, J=7.4 Hz), 8.05 (2H, d, J=7.4 Hz); $^{13}$C NMR (101 MHz, CDCl$_3$) δ 6.5, 7.0, 13.8, 18.0, 19.2, 22.6, 27.0, 27.1, 27.2, 30.5, 39.8, 42.2, 51.4, 55.4, 72.0, 78.8, 121.7, 128.4, 129.5, 132.7, 153.2, 166.4, 203.2; Exact mass (ESI) calculated for C$_{31}$H$_{49}$O$_4$Si ([M+H]$^+$) 513.3395, found 513.3405.

(22E)-Des-A,B-8β-benzoyloxy-24-hydroxy-25-[(triethylsilyl)oxy]-22-dehydrocholestan (4, Mixture of 24-Isomers)

To a stirred solution of 3 (200 mg; 0.39 mmol) in tetrahydrofuran (1.5 ml) and ethanol (4.5 ml) CeCl$_3$×7H$_2$O (298 mg; 0.80 mmol) and NaBH$_4$ (46 mg; 1.20 mmol) was added at 0° C. After 30 min. saturated aqueous solution of NH$_4$Cl (2 ml) and water (5 ml) were added and the mixture was extracted with methylene dichloride (3×40 ml). Organic phase was dried over anhydrous Na$_2$SO$_4$, concentrated under reduced pressure and the residue was purified by column chromatography (5-15% ethyl acetate/hexane) to give 180 mg (0.35 mmol; 90% yield) of 4 as a mixture of 24-diastereoisomers. Exact mass (ESI) calculated for C$_{31}$H$_{50}$O$_4$SiNa ([M+Na]$^+$) 537.3371, found 537.3380.

(22E)-Des-A,B-8β-benzoyloxy-24,25-di-[(triethylsilyl)oxy]-22-dehydrocholestan (5, Mixture of 24-Isomers)

To a stirred solution of 4 (150 mg; 0.29 mmol) and 2,6-lutidine (67 µl; 62 mg; 0.58 mmol) in methylene dichloride (1 ml) triethylsilyl trifluoromethanesulfonate (79 µl; 92 mg; 0.35 mmol) was added dropwise at −50° C. After 20 min. wet methylene dichloride (1 ml) and water (5 ml) was added and the mixture was extracted with methylene dichloride (3×25 ml). Organic phase was dried over anhydrous Na$_2$SO$_4$ and concentrated under reduced pressure. The residue was purified by column chromatography (hexane—3% ethyl acetate/hexane) to give 165 mg (0.26 mmol; 90% yield) of 5. Exact mass (ESI) calculated for C$_{37}$H$_{64}$O$_4$Si$_2$Na ([M+Na]$^+$) 651.4236, found 651.4234.

(22E)-Des-A,B-24,25-di-[(triethylsilyl)oxy]-22-dehydrocholestan-8β-ol (6, Mixture of 24-isomers)

A solution of 5 (160 mg; 0.25 mmol) in tetrahydrofuran (3 ml) was treated with a 3 M solution of methylmagnesium bromide in diethyl ether (750 µl; 2.25 mmol) for 5 h at 0° C. Saturated aqueous solution of NH$_4$Cl (2 ml), brine (2 ml) and water (5 ml) was carefully added and the mixture was extracted with methylene dichloride (3×25 ml). Organic phase was dried over anhydrous Na$_2$SO$_4$ and concentrated under reduced pressure. The residue was purified on a silica gel Sep-Pack cartridge (5-15% ethyl acetate/hexane) to give 106 mg (0.20 mmol; 81% yield) of 6. Exact mass (ESI) calculated for C$_{30}$H$_{60}$O$_3$Si$_2$Na ([M+Na]$^+$) 547.3974, found 547.3957.

(22E)-Des-A,B-24,25-di-[(triethylsilyl)oxy]-22-dehydrocholestan-8-one (7, Mixture of 24-Isomers)

A solution of 6 (65 mg; 120 µmol) and pyridinium p-toluenesulfonate (2 crystals) in methylene dichloride (6 ml) was treated with pyridinium dichromate (150 mg; 400 µmol) for 3 h. The mixture was purified on a silica gel Sep-Pack cartridge (3-7% ethyl acetate/hexane) to give 54 mg (103 µmol; 86%) of 7. Exact mass (ESI) calculated for C$_{30}$H$_{58}$O$_3$Si$_2$Na ([M+Na]$^+$) 545.3817, found 545.3817.

(22E)-(24R)-2-Methylene-22-dehydro-1α,24,25-trihydroxy-19-norvitamin D$_3$ (10, WT-51) and (22E)-(24S)-2-Methylene-22-dehydro-1α,24,25-trihydroxy-19-norvitamin D$_3$ (11, WT-52)

To a stirred solution of 8 (87 mg; 150 µmol) in tetrahydrofuran (1.5 ml) two drops of 1.8 M phenyl lithium solution in di-n-butyl ether was added at −25° C. and the solution turned deep orange. Then stoichiometric amount of phenyl lithium solution (78 µl; 140 µmol) was added dropwise. After 20 min. the mixture was cooled to −78° C. and a solution of 7 (53 mg; 101 µmol) in tetrahydrofuran (0.75 ml) was transferred via cannula. The mixture was stirred for 2 h, warmed to 0° C. and stirred for next 2 h. Saturated aqueous solution of NH$_4$Cl (1 ml), brine (1 ml) and water (5 ml) was carefully added and the mixture was extracted with hexane (3×25 ml). Organic phase was dried over Na$_2$SO$_4$ and concentrated under reduced pressure. The residue was purified on a silica gel Sep-Pack cartridge (hexane—2% ethyl acetate/hexane) to give 90 mg of crude 9. Crude 9 was dissolved in acetonitrile (2 ml) and treated with (±)-camphor-10-sulfonic acid (40 mg; 172 µmol) for 2 days. The mixture was purified on a previously treated with 10 drops of triethylamine silica gel Sep-Pack cartridge (10-30% 2-propanol/hexane) to give 28 mg (65 µmol; 64% yield from 7) of 10 and 11 as a mixture of diastereoisomers. The mixture was separated on HPLC (15% water/methanol; Zorbax-Eclipse XDB C18 5 µm; 3.5 ml/min.; R$_f$=5.30 min. for 10 and R$_f$=5.80 min. for 11) to give 9.5 mg (22 µmol; 22% yield from 7) of 10 and 13.5 mg (31 µmol; 31% yield from 7) of 11. X-ray analysis of 11 has shown 24S configuration. 10: UV (EtOH) λ$_{max}$=245, 252, 262 nm; $^1$H NMR (500 MHz, CD$_3$OD) δ 0.60 (3H, s), 1.07 (3H, d, J=6.6 Hz), 2×1.13 (3H each, s), 2.25-2.31 (2H, m), 2.48 (1H, dd, J=13.4 Hz, J=3.8 Hz), 2.66 (1H, dd, J=13.2 Hz, J=4.3 Hz), 2.85 (1H, dd, J=12.2 Hz, J=3.8 Hz), 3.73 (1H, d, J=7.4 Hz), 4.37 (1H, m), 4.41 (1H, m), 5.04 (1H, s), 5.05 (1H, s), 5.43 (1H, dd, J=15.4 Hz, J=7.5 Hz), 5.52 (1H, dd, J=15.4 Hz, J=8.6 Hz), 5.90 (1H, d, J=11.1 Hz), 6.26 (1H, d, J=11.1 Hz); 11: UV (EtOH) λ$_{max}$=244, 252, 261 nm; 1H NMR (500 MHz, CD$_3$OD) δ 0.60 (3H, s), 1.06 (3H, d, J=6.6 Hz), 1.12 (3H, s), 1.13 (3H, s), 1.65-1.70 (2H, m), 1.79-1.83 (1H, m), 1.93-2.07 (2H, m), 2.13 (1H, m), 2.25-2.31 (2H, m), 2.48 (1H, dd, J=13.3 Hz, J=3.9 Hz), 2.67 (1H, dd, J=13.2 Hz, J=4.3 Hz), 2.85 (1H, dd, J=12.2 Hz, J=3.7 Hz), 3.75 (1H, d, J=6.7 Hz), 4.37 (1H, m), 4.41 (1H, m), 5.04 (1H, s), 5.06 (1H, s), 5.45 (1H, dd, J=15.4 Hz, J=6.9 Hz), 5.57 (1H, dd, J=15.4 Hz, J=8.4 Hz), 5.90 (1H, d, J=11.1 Hz), 6.26 (1H, d, J=11.1 Hz); MS (EI) m/z 430 (M$^+$, 10), 396 (7), 253 (22), 91 (100); exact mass (ESI) calculated for C$_{27}$H$_{42}$O$_4$Na ([M+Na]$^+$) 453.2976, found 453.2977.

Scheme I.

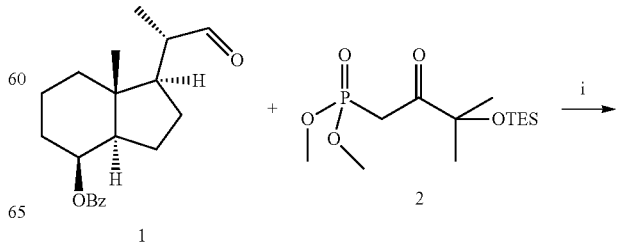

9

-continued

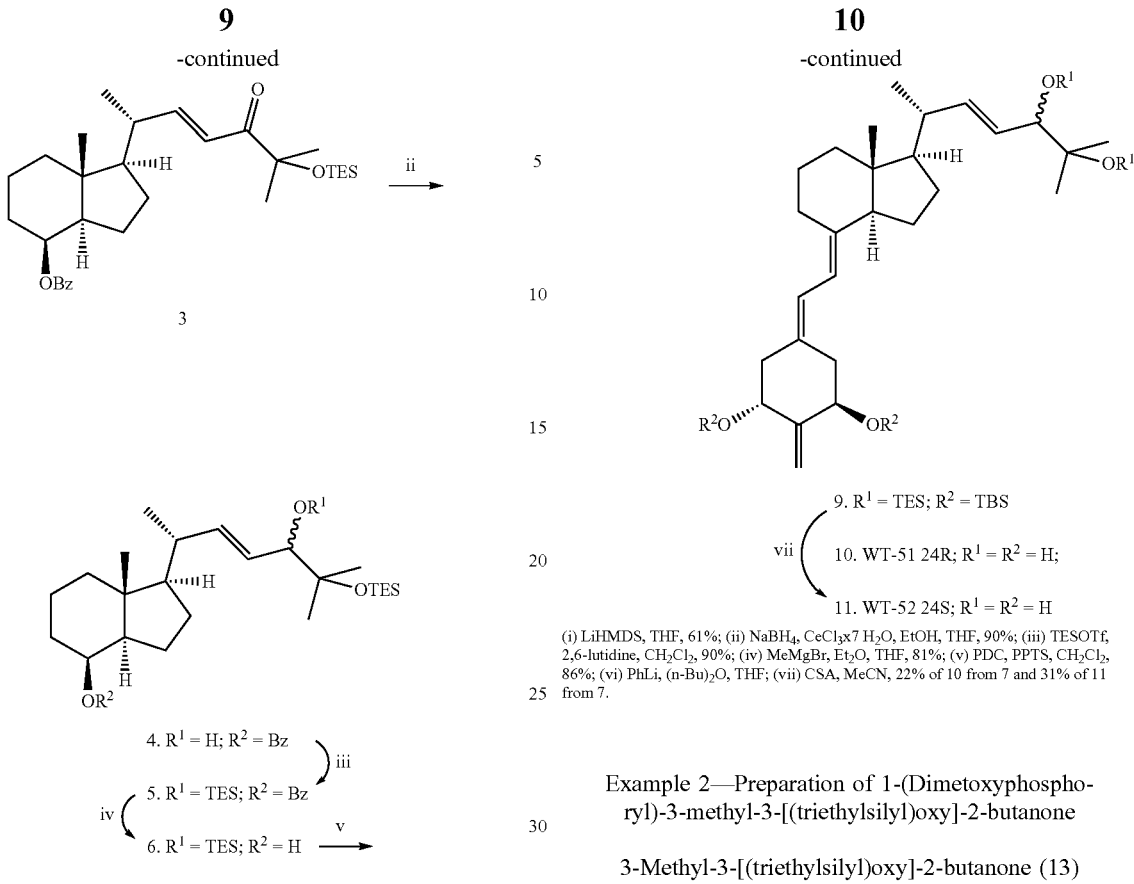

4. $R^1 = H; R^2 = Bz$
5. $R^1 = TES; R^2 = Bz$
6. $R^1 = TES; R^2 = H$

Scheme I (continued).

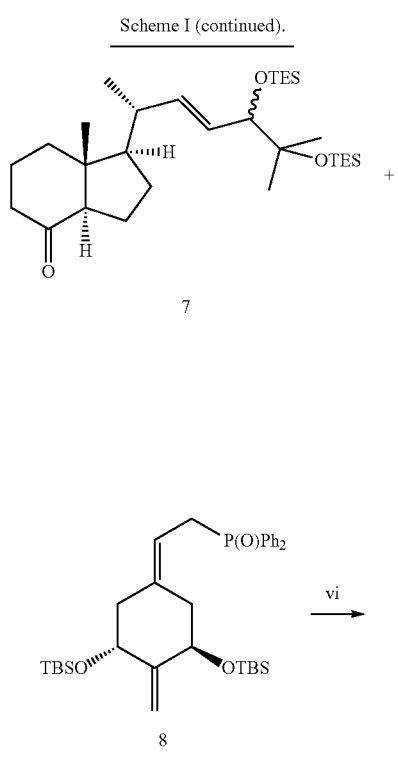

10

-continued

9. $R^1 = TES; R^2 = TBS$
10. WT-51 24R; $R^1 = R^2 = H$;
11. WT-52 24S; $R^1 = R^2 = H$ (i) LiHMDS, THF, 61%; (ii) NaBH$_4$, CeCl$_3$x7 H$_2$O, EtOH, THF, 90%; (iii) TESOTf, 2,6-lutidine, CH$_2$Cl$_2$, 90%; (iv) MeMgBr, Et$_2$O, THF, 81%; (v) PDC, PPTS, CH$_2$Cl$_2$, 86%; (vi) PhLi, (n-Bu)$_2$O, THF; (vii) CSA, MeCN, 22% of 10 from 7 and 31% of 11 from 7.

Example 2—Preparation of 1-(Dimetoxyphosphoryl)-3-methyl-3-[(triethylsilyl)oxy]-2-butanone 3-Methyl-3-[(triethylsilyl)oxy]-2-butanone (13)

To a stirred solution of 3-hydroxy-3-methyl-2-butanone (Scheme 2; 1.20 ml; 1.16 g; 11.4 mmol) and 2,6-lutidine (1.86 ml; 1.71 g; 16.0 mmol) in methylene dichloride (30 ml) triethylsilyl trifluoromethanesulfonate (3.11 ml; 3.61 g; 13.7 mmol) was added dropwise at −50° C. After 20 min. wet methylene dichloride (5 ml) and water (50 ml) was added and the mixture was extracted with methylene dichloride (3×100 ml). Organic phase was dried over anhydrous Na$_2$SO$_4$ and concentrated under reduced pressure. The residue was purified by column chromatography (hexane—3% ethyl acetate/hexane) to give 2.40 g (10.4 mmol; 91% yield) of 13. $^1$H NMR (500 MHz, CDCl$_3$) δ 0.63 (6H, q, J=7.9 Hz), 0.97 (9H, t, J=7.9 Hz), 1.33 (6H, s), 2.23 (3H, s); $^{13}$C NMR (126 MHz, CDCl$_3$) δ 6.5, 7.0, 27.0, 27.7, 79.7, 214.0; MS (EI) m/z 216 ([M−Et]$^+$, 100), 173 (81), 172 (30) 115 (68), 87 (67); exact mass calculated for C$_9$H$_{19}$O$_2$Si ([M−Et]$^+$) 187.1149, found 187.1144.

1-Bromo-3-methyl-3-[(triethylsilyl)oxy]-2-butanone (14)

To a stirred solution of 13 (2.40 g; 10.4 mmol) and triethylamine (2.92 ml; 2.12 g; 21.0 mmol) in methylene dichloride (50 ml) triethylsilyl trifluoromethanesulfonate (2.37 ml; 2.75 g; 10.4 mmol) was added dropwise at 0° C. After 15 min. N-bromosuccinimide (2.05 g; 11.5 mmol) was added and a cooling bath was removed. After 30 min. saturated aqueous solution of NH$_4$Cl (10 ml) and water (50 ml) was added and the mixture was extracted with methylene dichloride (3×100 ml). Organic phase was dried over anhydrous Na$_2$SO$_4$ and concentrated under reduced pressure. The residue was purified by column chromatography (hexane—5% ethyl acetate/hexane) to give 1.55 g (5.25 mmol; 50% yield) of 14. $^1$H NMR (400 MHz, CDCl$_3$) δ 0.64

(6H, q, J=7.9 Hz), 0.97 (9H, t, J=7.9 Hz), 1.41 (6H, s), 4.44 (2H, s); $^{13}$C NMR (101 MHz, CDCl$_3$) δ 6.5, 7.0, 27.8, 33.6, 80.4, 206.2; MS (EI) m/z 294 and 296 ([M−Et]$^+$, 24 and 23), 187 (45), 173 (100); exact mass calculated for C$_9$H$_{18}$O$_2$BrSi ([M−Et]$^{+)}$265.0254, found 265.0247.

1-(Dimetoxyphosphoryl)-3-methyl-3-[(triethylsilyl)oxy]-2-butanone (2)

A solution of 14 (1.55 g; 5.25 mmol) and trimethyl phosphite (514 µl; 782 mg; 6.31 mmol) in toluene (20 ml) was refluxed for 3 days. The mixture was purified by column chromatography (5-15% 2-propanol/hexane) to give 1.54 g (4.75 mmol; 90% yield) of 2. $^1$H NMR (400 MHz, CDCl$_3$) δ 0.65 (6H, q, J=7.9 Hz), 0.98 (9H, t, J=7.9 Hz), 1.36 (6H, s), 3.40 (2H, d, J$_{H-P}$=20.7 Hz) 3.80 (6H, d, J$_{H}$-P=11.2 Hz); $^{13}$C NMR (101 MHz, CDCl$_3$) δ 6.4, 6.9, 26.8, 33.7 (d, J$_{C-P}$=137.8 Hz), 52.8 (d, J$_{C-P}$=6.7 Hz) 80.0, 207.1 (d, J$_{C-P}$=6.0 Hz); MS (EI) m/z 324 ([M−Et]$^+$, 98), 238 (65), 211 (61), 173 (100); exact mass calculated for C$_{11}$H$_{24}$O$_5$PSi ([M−Et]$^+$) 295.1126, found 295.1126.

Scheme II.

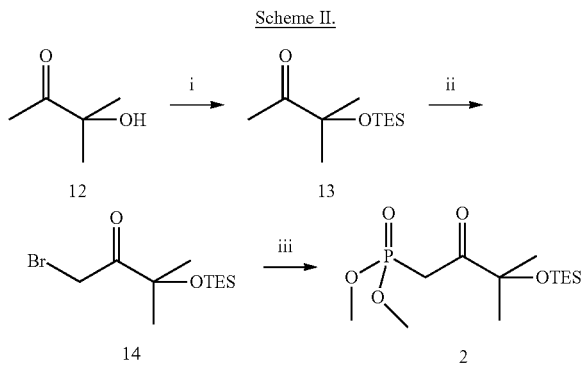

(i) TESOTf, 2,6-lutidine, CH$_2$Cl$_2$, 91%; (ii) TESOTf, Et$_3$N, CH$_2$Cl$_2$; NBS, 50%; (iii) P(OMe)$_3$, PhMe, 90%.

Example 3—Crystallization of (22E)-(24R)-2-methylene-22-dehydro-1α,24,25-trihydroxy-19-nor-vitamin D$_3$ (WT-51) and X-ray Diffraction Analysis Crystallization of (22E)-(24R)-2-methylene-22-dehydro-1α,24,25-trihydroxy-19-nor-vitamin D$_3$ (WT-51) from Ethyl Acetate/Hexane WT-51 (15 mg) was placed in a 4 mL vial and dissolved in ethyl acetate (0.3 mL). Next, hexane (1 mL) was added dropwise to reach a saturation point. The vial then was sealed and left at room temperature. After about 1 hour, crystals began to grow and the mixture was left for the next 2 days at room temperature to obtain crystals. The obtained crystals were filtered off, and washed with a small volume of ethyl acetate/hexane, and dried to give crystalline WT-51.

Figure 2:
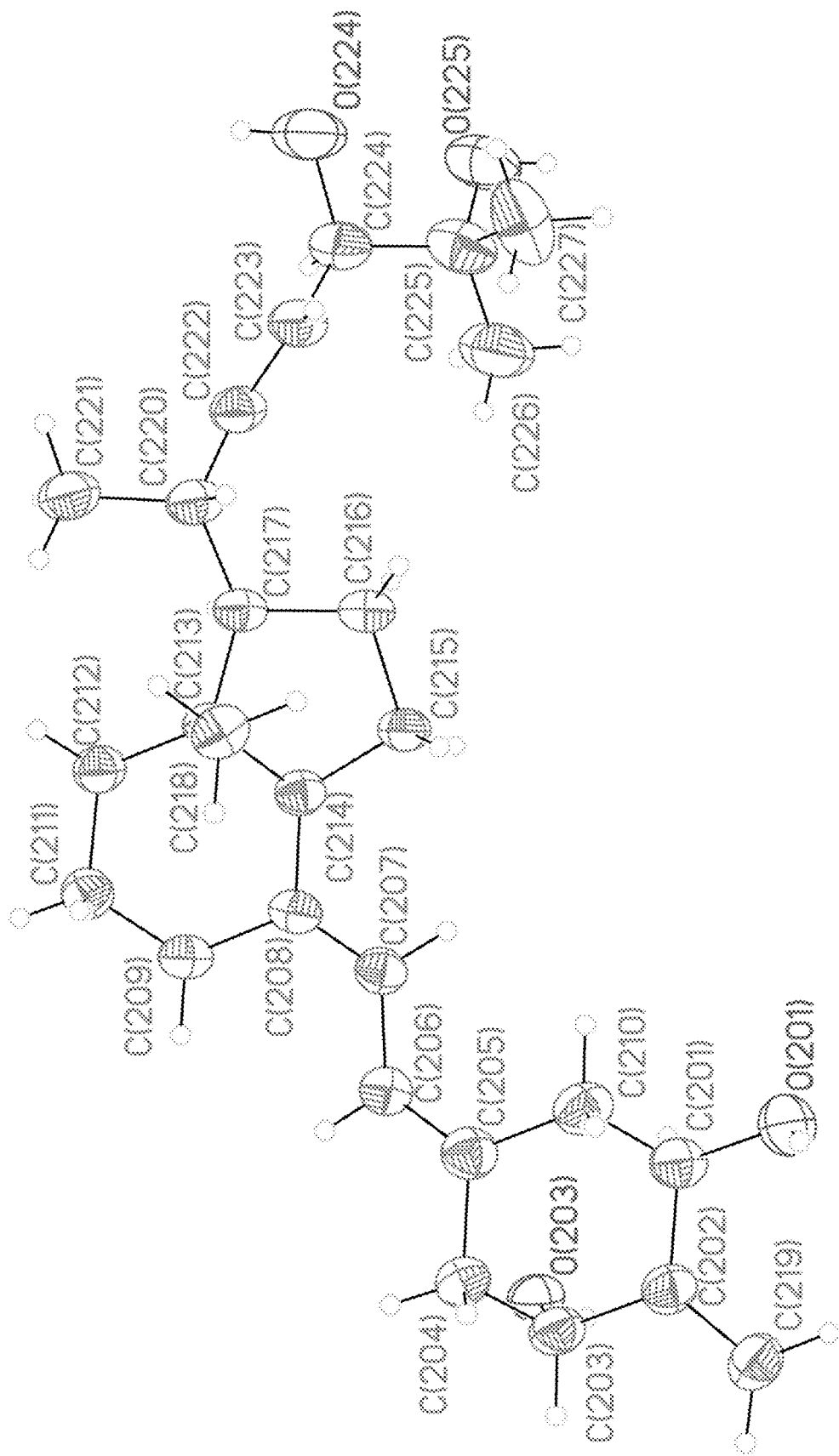
FIG. 2 is an illustration of one embodiment of a three dimensional molecular structure for WT-51 as defined by the atomic positional parameters discovered and set forth herein.
Figure 3:
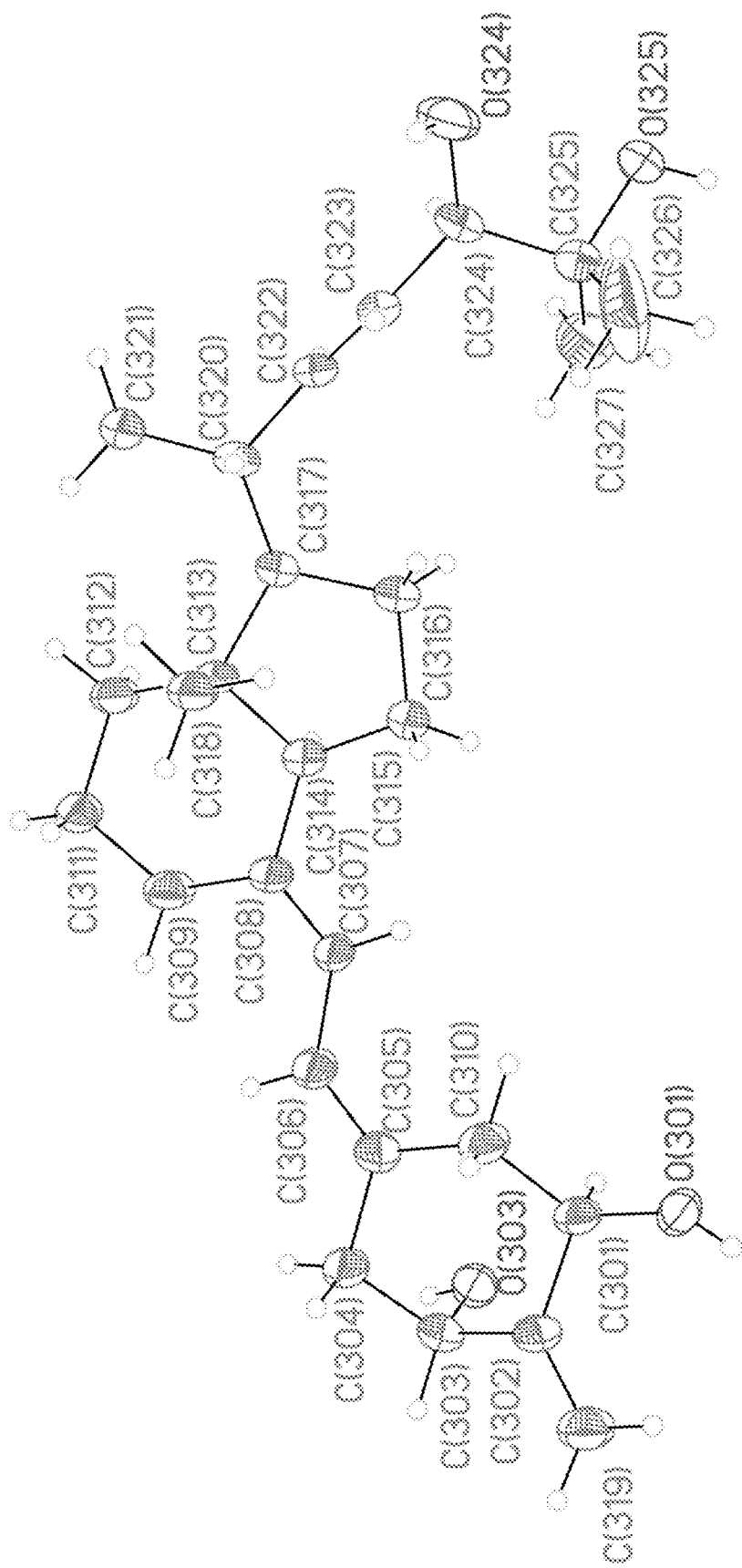
FIG. 3 is an illustration of one embodiment of a three dimensional molecular structure for WT-51 as defined by the atomic positional parameters discovered and set forth herein.
Figure 4:
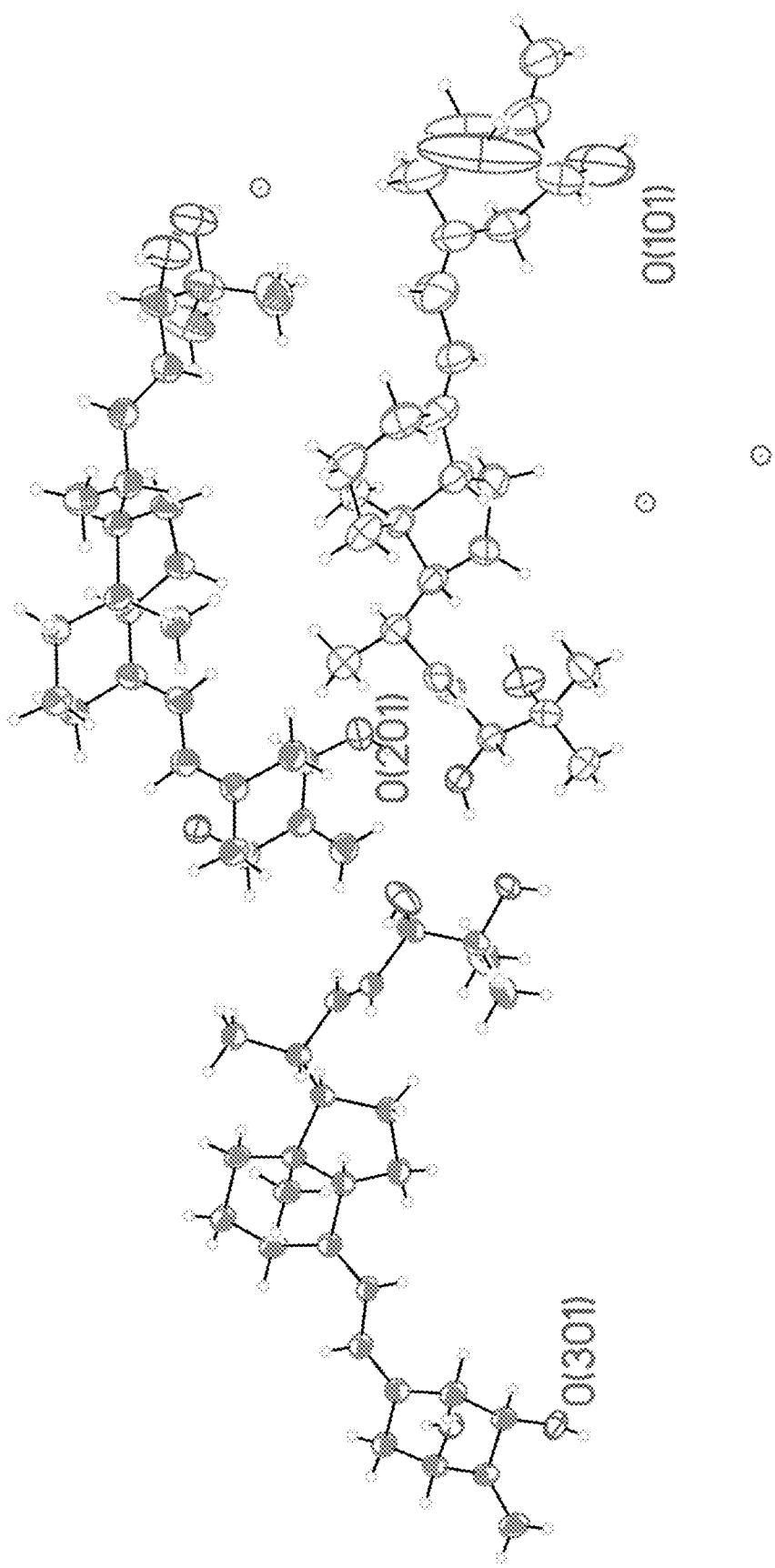
FIG. 4 is an illustration of three dimensional molecular structures for WT-51 as defined by the atomic positional parameters discovered and set forth herein.

Experimental. The crystals thus obtained were suitable for X-ray diffraction analysis and were analyzed accordingly. (See, e.g., U.S. Pat. Nos. 9,212,137; 9,040,729; 8,940,916; 8,884,039; 8,519,169; 8,420,839; and 8,404,874; the contents of which are incorporated herein by reference in their entireties). Crystal data and structure refinement are provided in Table 1. Atomic coordinates (Å×10$^4$) and equivalent isotropic displacement parameters (Å$^2$×10$^3$) are provided in Table 2. Bond lengths [Å] and angles [º] are provided in Table 3. Anisotropic displacement parameters (Å$^2$×10$^3$) are provided in Table 4. Hydrogen coordinates (Å×10$^4$) and isotropic displacement parameters (Å$^2$×10$^3$) are provided in Table 5. Torsion angles [º] are provided in Table 6. The three dimensional structure of WT-51 as defined by the physical data and atomic positional parameters disclosed in Table 1-6 is illustrated in FIGS. 1-4.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of references are made herein. The cited references are incorporated by reference herein in their entireties. In the event that there is an inconsistency between a definition of a term in the specification as compared to a definition of the term in a cited reference, the term should be interpreted based on the definition in the specification.

TABLE 1

| Crystal data and structure refinement. | |
|---|---|
| Empirical formula | C27 H42 O4•1.33 H2O |
| Formula weight | 454, 430.62 without H20 |
| Temperature | 100(2) K |
| Wavelength | 1.54178 Å |
| Crystal system | Monoclinic |
| Space group | P2$_1$ |
| Unit cell dimensions | a = 16.3058(9) Å    α = 90° |
| | b = 10.0461(6) Å    β = 109.001(3)° |
| | c = 26.0527(15) Å   γ = 90° |
| Volume | 4035.1(4) Å$^3$ |
| Z | 6 |
| Density (calculated) | 1.076 Mg/m$^3$ |
| Absorption coefficient | 0.561 mm$^{-1}$ |
| F(000) | 1430 |
| Crystal size | 0.05 × 0.04 × 0.3 mm |
| Theta range for data collection | 2.843 to 62.415° |
| Index ranges | −17 <= h <= 18, −11 <= k <= 11, −29 <= l <= 29 |
| Reflections collected | 32723 |
| Independent reflections | 12241 [R(int) = 0.0582] |
| Completeness to theta = 62.415∞ | 98.4% |
| Absorption correction | None |
| Refinement method | Full-matrix least-squares on F$^2$ |
| Data/restraints/parameters | 12241/1/874 |
| Goodness-of-fit on F$^2$ | 0.975 |
| Final R indices [I > 2sigma(I)] | R1 = 0.0790, wR2 = 0.2184 |
| R indices (all data) | R1 = 0.1014, wR2 = 0.2408 |
| Absolute structure parameter | −0.17(18) |
| Extinction coefficient | n/a |
| Largest diff. peak and hole | 0.567 and −0.300 e/Å$^3$ |

TABLE 2

Atomic coordinates (Å × 10⁴) and equivalent isotropic displacement parameters (Å² × 10³).
U(eq) is defined as one third of the trace of the orthogonalized $U_{ij}$ tensor.

| | x | y | z | U(eq) |
|---|---|---|---|---|
| O(301) | 6552(3) | 2722(4) | 428(2) | 49(1) |
| O(303) | 4579(3) | 5562(4) | −120(2) | 46(1) |
| O(325) | 11671(3) | 5441(5) | −2184(2) | 53(1) |
| O(203) | 11026(3) | 12936(5) | −2518(2) | 57(1) |
| C(313) | 8967(4) | 9428(6) | −546(2) | 38(1) |
| O(124) | 11921(4) | 7064(5) | −2990(3) | 72(2) |
| C(304) | 5725(4) | 6688(7) | 611(3) | 44(2) |
| O(201) | 11630(4) | 9648(5) | −3406(2) | 66(1) |
| C(307) | 7340(4) | 7516(6) | −145(3) | 39(1) |
| O(324) | 12479(3) | 7376(6) | −1520(2) | 75(2) |
| C(308) | 7586(4) | 8560(6) | −379(3) | 40(1) |
| C(301) | 6137(4) | 4013(6) | 306(3) | 41(1) |
| C(314) | 8188(4) | 8424(6) | −713(3) | 44(1) |
| C(305) | 6433(4) | 6501(7) | 367(3) | 43(1) |
| C(208) | 14684(7) | 13712(7) | −2040(3) | 47(2) |
| C(322) | 10647(4) | 8846(6) | −1325(3) | 43(2) |
| O(225) | 18480(5) | 13560(8) | −4317(3) | 94(2) |
| C(318) | 9576(4) | 9160(7) | 29(3) | 43(1) |
| C(206) | 13318(4) | 12615(7) | −2010(3) | 50(2) |
| C(323) | 11278(4) | 7972(6) | −1240(3) | 43(2) |
| C(302) | 5481(4) | 4256(6) | 596(3) | 41(1) |
| C(201) | 11723(5) | 10653(7) | −3010(3) | 55(2) |
| C(324) | 11554(7) | 7334(7) | −1682(3) | 46(2) |
| C(306) | 6697(4) | 7526(6) | 129(3) | 42(1) |
| C(207) | 14030(4) | 12840(7) | −2223(3) | 48(2) |
| C(309) | 7254(4) | 9950(7) | −395(3) | 49(2) |
| C(311) | 7985(4) | 11008(7) | −264(3) | 47(2) |
| C(214) | 15368(4) | 13883(7) | −2298(3) | 45(2) |
| C(303) | 5043(4) | 5572(6) | 453(3) | 42(1) |
| C(312) | 8602(4) | 10837(6) | −598(3) | 45(2) |
| C(320) | 10347(4) | 9470(6) | −892(3) | 43(1) |
| C(116) | 15160(5) | 6779(7) | −3503(3) | 59(2) |
| C(213) | 16311(4) | 13705(6) | −1905(3) | 47(2) |
| C(217) | 16828(4) | 13959(7) | −2303(3) | 47(2) |
| C(122) | 14092(5) | 7380(8) | −2811(3) | 60(2) |
| C(310) | 6822(4) | 5116(6) | 441(3) | 45(2) |
| C(218) | 16451(4) | 12268(7) | −1694(3) | 52(2) |
| C(215) | 15340(4) | 13101(7) | −2801(3) | 51(2) |
| C(316) | 9336(4) | 7469(7) | −984(3) | 53(2) |
| C(224) | 18653(9) | 13644(9) | −3389(3) | 65(2) |
| C(204) | 12028(5) | 11528(8) | −1886(3) | 58(2) |
| C(317) | 9419(4) | 9013(6) | −966(3) | 40(1) |
| C(205) | 12722(5) | 11644(7) | −2149(3) | 54(2) |
| O(224) | 19531(4) | 13319(8) | −3334(3) | 92(2) |
| C(321) | 10433(5) | 10985(7) | −917(3) | 53(2) |
| C(202) | 11033(5) | 10607(7) | −2746(3) | 51(2) |
| C(221) | 18384(5) | 14028(9) | −1629(3) | 65(2) |
| C(222) | 18099(4) | 13898(7) | −2615(3) | 56(2) |
| C(211) | 15769(5) | 14574(8) | −1157(3) | 55(2) |
| C(216) | 16251(4) | 13334(8) | −2844(3) | 52(2) |
| C(203) | 11129(5) | 11614(7) | −2305(3) | 55(2) |
| C(315) | 8600(5) | 7119(7) | −756(4) | 56(2) |
| O(125) | 11863(4) | 6217(7) | −4057(3) | 87(2) |
| C(123) | 13277(5) | 7328(7) | −3136(3) | 57(2) |
| C(209) | 14825(4) | 14636(7) | −1557(3) | 50(2) |
| C(219) | 10387(5) | 9739(8) | −2883(3) | 62(2) |
| C(223) | 18421(4) | 13128(8) | −2917(3) | 57(2) |
| C(220) | 17787(4) | 13490(7) | −2159(3) | 52(2) |
| C(113) | 16305(5) | 8318(8) | −3020(3) | 59(2) |
| C(319) | 5296(4) | 3395(8) | 927(3) | 54(2) |
| C(212) | 16454(5) | 14718(7) | −1443(3) | 52(2) |
| C(124) | 12621(5) | 6367(7) | −3085(3) | 58(2) |
| C(109) | 18167(6) | 8135(12) | −2900(4) | 84(3) |
| C(118) | 15998(6) | 9540(8) | −3386(4) | 67(2) |
| C(210) | 12638(5) | 10600(8) | −2584(3) | 58(2) |
| C(120) | 14783(5) | 8325(8) | −2834(3) | 60(2) |
| C(325) | 11230(5) | 5933(7) | −1819(4) | 62(2) |
| C(117) | 15515(5) | 7568(7) | −2960(3) | 56(2) |
| C(114) | 16688(5) | 7251(8) | −3298(3) | 61(2) |
| C(125) | 12262(6) | 5423(9) | −3583(3) | 67(2) |
| C(115) | 15894(5) | 6740(9) | −3762(4) | 70(2) |
| C(112) | 17014(6) | 8704(9) | −2482(4) | 74(2) |
| C(108) | 17490(5) | 7676(9) | −3420(4) | 71(2) |
| C(327) | 10241(6) | 6013(11) | −2169(5) | 92(3) |
| C(225) | 18085(6) | 13090(11) | −3935(4) | 80(3) |
| C(121) | 15094(6) | 9096(9) | −2289(4) | 76(2) |
| C(326) | 11405(15) | 5040(10) | −1354(6) | 167(9) |
| C(110) | 18041(6) | 7167(12) | −4961(5) | 96(3) |
| C(106) | 18316(7) | 8145(14) | −4050(6) | 111(4) |
| C(105) | 18494(7) | 8022(12) | −4501(4) | 88(3) |
| C(126) | 12992(7) | 4649(11) | −3681(4) | 89(3) |
| C(107) | 17582(6) | 7649(10) | −3906(4) | 77(2) |
| C(227) | 18119(9) | 11566(12) | −3930(5) | 109(4) |
| C(127) | 11601(8) | 4481(10) | −3500(5) | 98(3) |
| C(226) | 17180(7) | 13662(16) | −4092(5) | 111(4) |
| C(102) | 19431(7) | 6890(12) | −5163(6) | 101(4) |
| C(111) | 17838(7) | 9140(12) | −2587(4) | 99(4) |
| C(119) | 19688(8) | 6800(13) | −5578(6) | 108(4) |
| C(103) | 19834(7) | 7840(30) | −4706(6) | 172(10) |
| O(101) | 18130(18) | 5540(30) | −5610(11) | 430(20) |
| C(104) | 19200(9) | 8823(19) | −4595(6) | 139(6) |
| C(101) | 18663(11) | 6117(17) | −5085(9) | 150(7) |
| O(103) | 20288(7) | 7240(30) | −4191(5) | 353(19) |
| O(2) | 16200(20) | 15120(70) | −5679(17) | 630(50) |
| O(1) | 17476(7) | 12886(13) | −5340(4) | 145(4) |
| O(3) | 14250(30) | 3980(130) | −4710(20) | 890(110) |
| O(4) | 15000(40) | 830(100) | −4827(11) | 960(100) |

TABLE 3

Bond lengths [Å] and angles [°].

| | |
|---|---|
| O(301)—C(301) | 1.449(8) |
| O(301)—H(30A) | 0.8400 |
| O(303)—C(303) | 1.439(8) |
| O(303)—H(30B) | 0.8400 |
| O(325)—C(325) | 1.451(8) |
| O(325)—H(32A) | 0.8400 |
| O(203)—C(203) | 1.428(9) |
| O(203)—H(20A) | 0.8400 |
| C(313)—C(312) | 1.524(9) |
| C(313)—C(318) | 1.526(9) |
| C(313)—C(317) | 1.562(8) |
| C(313)—C(314) | 1.569(8) |
| O(124)—C(124) | 1.427(9) |
| O(124)—H(12A) | 0.8400 |
| C(304)—C(305) | 1.500(9) |
| C(304)—C(303) | 1.538(9) |
| C(304)—H(30C) | 0.9900 |
| C(304)—H(30D) | 0.9900 |
| O(201)—C(201) | 1.417(9) |
| O(201)—H(20B) | 0.8400 |
| C(307)—C(308) | 1.338(9) |
| C(307)—C(306) | 1.448(8) |
| C(307)—H(30E) | 0.9500 |
| O(324)—C(324) | 1.428(8) |
| O(324)—H(32B) | 0.8400 |
| C(308)—C(309) | 1.493(9) |
| C(308)—C(314) | 1.515(8) |
| C(301)—C(302) | 1.518(8) |
| C(301)—C(310) | 1.530(9) |
| C(301)—H(30F) | 1.0000 |
| C(314)—C(315) | 1.494(9) |
| C(314)—H(31A) | 1.0000 |
| C(305)—C(306) | 1.342(9) |
| C(305)—C(310) | 1.515(10) |
| C(208)—C(207) | 1.342(10) |
| C(208)—C(214) | 1.488(9) |
| C(208)—C(209) | 1.521(10) |
| C(322)—C(323) | 1.316(9) |
| C(322)—C(320) | 1.503(9) |
| C(322)—H(32C) | 0.9500 |
| O(225)—C(225) | 1.430(11) |
| O(225)—H(22A) | 0.8400 |
| C(318)—H(31B) | 0.9800 |

TABLE 3-continued

Bond lengths [Å] and angles [°].

| | |
|---|---|
| C(318)—H(31C) | 0.9800 |
| C(318)—H(31D) | 0.9800 |
| C(206)—C(205) | 1.340(10) |
| C(206)—C(207) | 1.459(9) |
| C(206)—H(20C) | 0.9500 |
| C(323)—C(324) | 1.510(9) |
| C(323)—H(32D) | 0.9500 |
| C(302)—C(319) | 1.324(9) |
| C(302)—C(303) | 1.491(9) |
| C(201)—C(202) | 1.498(10) |
| C(201)—C(210) | 1.543(10) |
| C(201)—H(20D) | 1.0000 |
| C(324)—C(325) | 1.506(10) |
| C(324)—H(32E) | 1.0000 |
| C(306)—H(30G) | 0.9500 |
| C(207)—H(20E) | 0.9500 |
| C(309)—C(311) | 1.550(9) |
| C(309)—H(30H) | 0.9900 |
| C(309)—H(30I) | 0.9900 |
| C(311)—C(312) | 1.539(9) |
| C(311)—H(31E) | 0.9900 |
| C(311)—H(31F) | 0.9900 |
| C(214)—C(215) | 1.514(10) |
| C(214)—C(213) | 1.555(9) |
| C(214)—H(21A) | 1.0000 |
| C(303)—H(30J) | 1.0000 |
| C(312)—H(31G) | 0.9900 |
| C(312)—H(31H) | 0.9900 |
| C(320)—C(321) | 1.531(10) |
| C(320)—C(317) | 1.533(8) |
| C(320)—H(32F) | 1.0000 |
| C(116)—C(115) | 1.553(11) |
| C(116)—C(117) | 1.560(11) |
| C(116)—H(11A) | 0.9900 |
| C(116)—H(11B) | 0.9900 |
| C(213)—C(212) | 1.535(10) |
| C(213)—C(218) | 1.535(10) |
| C(213)—C(217) | 1.555(9) |
| C(217)—C(216) | 1.551(10) |
| C(217)—C(220) | 1.557(9) |
| C(217)—H(21B) | 1.0000 |
| C(122)—C(123) | 1.323(11) |
| C(122)—C(120) | 1.489(11) |
| C(122)—H(12B) | 0.9500 |
| C(310)—H(31I) | 0.9900 |
| C(310)—H(31J) | 0.9900 |
| C(218)—H(21C) | 0.9800 |
| C(218)—H(21D) | 0.9800 |
| C(218)—H(21E) | 0.9800 |
| C(215)—C(216) | 1.544(9) |
| C(215)—H(21F) | 0.9900 |
| C(215)—H(21G) | 0.9900 |
| C(316)—C(315) | 1.542(9) |
| C(316)—C(317) | 1.556(10) |
| C(316)—H(31K) | 0.9900 |
| C(316)—H(31L) | 0.9900 |
| C(224)—O(224) | 1.429(10) |
| C(224)—C(223) | 1.492(11) |
| C(224)—C(225) | 1.528(13) |
| C(224)—H(22B) | 1.0000 |
| C(204)—C(205) | 1.506(10) |
| C(204)—C(203) | 1.519(11) |
| C(204)—H(20F) | 0.9900 |
| C(204)—H(20G) | 0.9900 |
| C(317)—H(31M) | 1.0000 |
| C(205)—C(210) | 1.517(11) |
| O(224)—H(22C) | 0.8400 |
| C(321)—H(32G) | 0.9800 |
| C(321)—H(32H) | 0.9800 |
| C(321)—H(32I) | 0.9800 |
| C(202)—C(219) | 1.324(10) |
| C(202)—C(203) | 1.501(10) |
| C(221)—C(220) | 1.507(11) |
| C(221)—H(22D) | 0.9800 |
| C(221)—H(22E) | 0.9800 |
| C(221)—H(22F) | 0.9800 |
| C(222)—C(223) | 1.327(10) |
| C(222)—C(220) | 1.495(10) |
| C(222)—H(22G) | 0.9500 |
| C(211)—C(212) | 1.539(10) |
| C(211)—C(209) | 1.554(10) |
| C(211)—H(21H) | 0.9900 |
| C(211)—H(21I) | 0.9900 |
| C(216)—H(21J) | 0.9900 |
| C(216)—H(21K) | 0.9900 |
| C(203)—H(20H) | 1.0000 |
| C(315)—H(31N) | 0.9900 |
| C(315)—H(31O) | 0.9900 |
| O(125)—C(125) | 1.437(11) |
| O(125)—H(12C) | 0.8400 |
| C(123)—C(124) | 1.477(11) |
| C(123)—H(12D) | 0.9500 |
| C(209)—H(20I) | 0.9900 |
| C(209)—H(20J) | 0.9900 |
| C(219)—H(21L) | 0.9500 |
| C(219)—H(21M) | 0.9500 |
| C(223)—H(22H) | 0.9500 |
| C(220)—H(22I) | 1.0000 |
| C(113)—C(114) | 1.536(12) |
| C(113)—C(118) | 1.535(11) |
| C(113)—C(116) | 1.549(12) |
| C(113)—C(117) | 1.544(11) |
| C(319)—H(31P) | 0.9500 |
| C(319)—H(31Q) | 0.9500 |
| C(212)—H(21O) | 0.9900 |
| C(212)—H(21P) | 0.9900 |
| C(124)—C(125) | 1.558(12) |
| C(124)—H(12E) | 1.0000 |
| C(109)—C(111) | 1.503(17) |
| C(109)—C(108) | 1.515(13) |
| C(109)—H(10A) | 0.9900 |
| C(109)—H(10B) | 0.9900 |
| C(118)—H(11C) | 0.9800 |
| C(118)—H(11D) | 0.9800 |
| C(118)—H(11E) | 0.9800 |
| C(210)—H(21Q) | 0.9900 |
| C(210)—H(21R) | 0.9900 |
| C(120)—C(117) | 1.539(11) |
| C(120)—C(121) | 1.550(12) |
| C(120)—H(12F) | 1.0000 |
| C(325)—C(326) | 1.460(15) |
| C(325)—C(327) | 1.574(13) |
| C(117)—H(11F) | 1.0000 |
| C(114)—C(108) | 1.505(11) |
| C(114)—C(115) | 1.544(11) |
| C(114)—H(11G) | 1.0000 |
| C(125)—C(127) | 1.502(13) |
| C(125)—C(126) | 1.513(13) |
| C(115)—H(11H) | 0.9900 |
| C(115)—H(11I) | 0.9900 |
| C(112)—C(111) | 1.520(14) |
| C(112)—H(11J) | 0.9900 |
| C(112)—H(11K) | 0.9900 |
| C(108)—C(107) | 1.323(13) |
| C(327)—H(32J) | 0.9800 |
| C(327)—H(32K) | 0.9800 |
| C(327)—H(32L) | 0.9800 |
| C(225)—C(226) | 1.511(14) |
| C(225)—C(227) | 1.531(16) |
| C(121)—H(12G) | 0.9800 |
| C(121)—H(12H) | 0.9800 |
| C(121)—H(12I) | 0.9800 |
| C(326)—H(32M) | 0.9800 |
| C(326)—H(32N) | 0.9800 |
| C(326)—H(32O) | 0.9800 |
| C(110)—C(105) | 1.463(16) |
| C(110)—C(101) | 1.569(18) |
| C(110)—H(11L) | 0.9900 |
| C(110)—H(11M) | 0.9900 |
| C(106)—C(105) | 1.306(16) |
| C(106)—C(107) | 1.453(14) |
| C(106)—H(10C) | 0.9500 |
| C(105)—C(104) | 1.489(15) |
| C(126)—H(12J) | 0.9800 |
| C(126)—H(12K) | 0.9800 |
| C(126)—H(12L) | 0.9800 |

TABLE 3-continued

Bond lengths [Å] and angles [°].

| | |
|---|---|
| C(107)—H(10D) | 0.9500 |
| C(227)—H(22J) | 0.9800 |
| C(227)—H(22K) | 0.9800 |
| C(227)—H(22L) | 0.9800 |
| C(127)—H(12M) | 0.9800 |
| C(127)—H(12N) | 0.9800 |
| C(127)—H(12O) | 0.9800 |
| C(226)—H(22M) | 0.9800 |
| C(226)—H(22N) | 0.9800 |
| C(226)—H(22O) | 0.9800 |
| C(102)—C(119) | 1.283(17) |
| C(102)—C(103) | 1.50(2) |
| C(102)—C(101) | 1.542(18) |
| C(111)—H(11N) | 0.9900 |
| C(111)—H(11O) | 0.9900 |
| C(119)—H(11P) | 0.9500 |
| C(119)—H(11Q) | 0.9500 |
| C(103)—O(103) | 1.436(18) |
| C(103)—C(104) | 1.52(3) |
| C(103)—H(10E) | 1.0000 |
| O(101)—C(101) | 1.48(3) |
| O(101)—H(10J) | 0.8400 |
| C(104)—H(10F) | 0.9900 |
| C(104)—H(10G) | 0.9900 |
| C(101)—H(10H) | 1.0000 |
| O(103)—H(10I) | 0.8400 |
| C(301)—O(301)—H(30A) | 109.5 |
| C(303)—O(303)—H(30B) | 109.5 |
| C(325)—O(325)—H(32A) | 109.5 |
| C(203)—O(203)—H(20A) | 109.5 |
| C(312)—C(313)—C(318) | 111.2(5) |
| C(312)—C(313)—C(317) | 116.4(5) |
| C(318)—C(313)—C(317) | 109.6(5) |
| C(312)—C(313)—C(314) | 108.3(5) |
| C(318)—C(313)—C(314) | 111.6(5) |
| C(317)—C(313)—C(314) | 99.1(5) |
| C(124)—O(124)—H(12A) | 109.5 |
| C(305)—C(304)—C(303) | 112.7(5) |
| C(305)—C(304)—H(30C) | 109.0 |
| C(303)—C(304)—H(30C) | 109.0 |
| C(305)—C(304)—H(30D) | 109.1 |
| C(303)—C(304)—H(30D) | 109.1 |
| H(30C)—C(304)—H(30D) | 107.8 |
| C(201)—O(201)—H(20B) | 109.5 |
| C(308)—C(307)—C(306) | 126.3(6) |
| C(308)—C(307)—H(30E) | 116.8 |
| C(306)—C(307)—H(30E) | 116.9 |
| C(324)—O(324)—H(32B) | 109.5 |
| C(307)—C(308)—C(309) | 125.9(5) |
| C(307)—C(308)—C(314) | 122.5(5) |
| C(309)—C(308)—C(314) | 111.3(5) |
| O(301)—C(301)—C(302) | 112.9(5) |
| O(301)—C(301)—C(310) | 110.1(5) |
| C(302)—C(301)—C(310) | 110.5(5) |
| O(301)—C(301)—H(30F) | 107.7 |
| C(302)—C(301)—H(30F) | 107.7 |
| C(310)—C(301)—H(30F) | 107.7 |
| C(315)—C(314)—C(308) | 120.9(6) |
| C(315)—C(314)—C(313) | 104.0(5) |
| C(308)—C(314)—C(313) | 113.6(5) |
| C(315)—C(314)—H(31A) | 105.7 |
| C(308)—C(314)—H(31A) | 105.7 |
| C(313)—C(314)—H(31A) | 105.7 |
| C(306)—C(305)—C(304) | 120.4(6) |
| C(306)—C(305)—C(310) | 125.4(6) |
| C(304)—C(305)—C(310) | 114.1(6) |
| C(207)—C(208)—C(214) | 122.7(6) |
| C(207)—C(208)—C(209) | 125.5(6) |
| C(214)—C(208)—C(209) | 111.7(6) |
| C(323)—C(322)—C(320) | 125.4(6) |
| C(323)—C(322)—H(32C) | 117.3 |
| C(320)—C(322)—H(32C) | 117.3 |
| C(225)—O(225)—H(22A) | 109.4 |
| C(313)—C(318)—H(31B) | 109.5 |
| C(313)—C(318)—H(31C) | 109.4 |
| H(31B)—C(318)—H(31C) | 109.5 |
| C(313)—C(318)—H(31D) | 109.5 |
| H(31B)—C(318)—H(31D) | 109.5 |

TABLE 3-continued

Bond lengths [Å] and angles [°].

| | |
|---|---|
| H(31C)—C(318)—H(31D) | 109.5 |
| C(205)—C(206)—C(207) | 127.4(7) |
| C(205)—C(206)—H(20C) | 116.3 |
| C(207)—C(206)—H(20C) | 116.3 |
| C(322)—C(323)—C(324) | 124.5(6) |
| C(322)—C(323)—H(32D) | 117.8 |
| C(324)—C(323)—H(32D) | 117.8 |
| C(319)—C(302)—C(303) | 123.3(6) |
| C(319)—C(302)—C(301) | 124.5(6) |
| C(303)—C(302)—C(301) | 112.2(5) |
| O(201)—C(201)—C(202) | 113.2(6) |
| O(201)—C(201)—C(210) | 110.4(6) |
| C(202)—C(201)—C(210) | 111.3(6) |
| O(201)—C(201)—H(20D) | 107.2 |
| C(202)—C(201)—H(20D) | 107.2 |
| C(210)—C(201)—H(20D) | 107.2 |
| O(324)—C(324)—C(325) | 110.7(6) |
| O(324)—C(324)—C(323) | 108.0(5) |
| C(325)—C(324)—C(323) | 114.1(6) |
| O(324)—C(324)—H(32E) | 108.0 |
| C(325)—C(324)—H(32E) | 108.0 |
| C(323)—C(324)—H(32E) | 107.9 |
| C(305)—C(306)—C(307) | 127.9(6) |
| C(305)—C(306)—H(30G) | 116.0 |
| C(307)—C(306)—H(30G) | 116.1 |
| C(208)—C(207)—C(206) | 127.2(6) |
| C(208)—C(207)—H(20E) | 116.4 |
| C(206)—C(207)—H(20E) | 116.4 |
| C(308)—C(309)—C(311) | 112.9(5) |
| C(308)—C(309)—H(30H) | 109.0 |
| C(311)—C(309)—H(30H) | 109.0 |
| C(308)—C(309)—H(30I) | 109.0 |
| C(311)—C(309)—H(30I) | 109.0 |
| H(30H)—C(309)—H(30I) | 107.8 |
| C(312)—C(311)—C(309) | 113.3(6) |
| C(312)—C(311)—H(31E) | 108.9 |
| C(309)—C(311)—H(31E) | 108.9 |
| C(312)—C(311)—H(31F) | 108.9 |
| C(309)—C(311)—H(31F) | 108.9 |
| H(31E)—C(311)—H(31F) | 107.7 |
| C(208)—C(214)—C(215) | 121.0(6) |
| C(208)—C(214)—C(213) | 114.5(5) |
| C(215)—C(214)—C(213) | 104.8(5) |
| C(208)—C(214)—H(21A) | 105.0 |
| C(215)—C(214)—H(21A) | 105.1 |
| C(213)—C(214)—H(21A) | 105.1 |
| O(303)—C(303)—C(302) | 107.4(5) |
| O(303)—C(303)—C(304) | 111.9(5) |
| C(302)—C(303)—C(304) | 109.5(5) |
| O(303)—C(303)—H(30J) | 109.4 |
| C(302)—C(303)—H(30J) | 109.4 |
| C(304)—C(303)—H(30J) | 109.4 |
| C(313)—C(312)—C(311) | 111.2(5) |
| C(313)—C(312)—H(31G) | 109.4 |
| C(311)—C(312)—H(31G) | 109.4 |
| C(313)—C(312)—H(31H) | 109.4 |
| C(311)—C(312)—H(31H) | 109.4 |
| H(31G)—C(312)—H(31H) | 108.0 |
| C(322)—C(320)—C(321) | 109.1(5) |
| C(322)—C(320)—C(317) | 109.3(5) |
| C(321)—C(320)—C(317) | 113.1(5) |
| C(322)—C(320)—H(32F) | 108.4 |
| C(321)—C(320)—H(32F) | 108.4 |
| C(317)—C(320)—H(32F) | 108.4 |
| C(115)—C(116)—C(117) | 107.2(6) |
| C(115)—C(116)—H(11A) | 110.3 |
| C(117)—C(116)—H(11A) | 110.2 |
| C(115)—C(116)—H(11B) | 110.3 |
| C(117)—C(116)—H(11B) | 110.3 |
| H(11A)—C(116)—H(11B) | 108.5 |
| C(212)—C(213)—C(218) | 112.0(6) |
| C(212)—C(213)—C(217) | 115.9(5) |
| C(218)—C(213)—C(217) | 110.1(6) |
| C(212)—C(213)—C(214) | 107.8(5) |
| C(218)—C(213)—C(214) | 110.1(5) |
| C(217)—C(213)—C(214) | 100.2(5) |
| C(213)—C(217)—C(216) | 103.8(5) |
| C(213)—C(217)—C(220) | 120.6(6) |

TABLE 3-continued

Bond lengths [Å] and angles [°].

| | |
|---|---|
| C(216)—C(217)—C(220) | 111.2(5) |
| C(213)—C(217)—H(21B) | 106.8 |
| C(216)—C(217)—H(21B) | 106.8 |
| C(220)—C(217)—H(21B) | 106.8 |
| C(123)—C(122)—C(120) | 128.0(7) |
| C(123)—C(122)—H(12B) | 116.0 |
| C(120)—C(122)—H(12B) | 115.9 |
| C(305)—C(310)—C(301) | 113.1(5) |
| C(305)—C(310)—H(31I) | 109.0 |
| C(301)—C(310)—H(31I) | 109.0 |
| C(305)—C(310)—H(31J) | 109.0 |
| C(301)—C(310)—H(31J) | 109.0 |
| H(31I)—C(310)—H(31J) | 107.8 |
| C(213)—C(218)—H(21C) | 109.5 |
| C(213)—C(218)—H(21D) | 109.5 |
| H(21C)—C(218)—H(21D) | 109.5 |
| C(213)—C(218)—H(21E) | 109.4 |
| H(21C)—C(218)—H(21E) | 109.5 |
| H(21D)—C(218)—H(21E) | 109.5 |
| C(214)—C(215)—C(216) | 103.1(5) |
| C(214)—C(215)—H(21F) | 111.1 |
| C(216)—C(215)—H(21F) | 111.1 |
| C(214)—C(215)—H(21G) | 111.2 |
| C(216)—C(215)—H(21G) | 111.2 |
| H(21F)—C(215)—H(21G) | 109.1 |
| C(315)—C(316)—C(317) | 106.7(5) |
| C(315)—C(316)—H(31K) | 110.4 |
| C(317)—C(316)—H(31K) | 110.4 |
| C(315)—C(316)—H(31L) | 110.4 |
| C(317)—C(316)—H(31L) | 110.4 |
| H(31K)—C(316)—H(31L) | 108.6 |
| O(224)—C(224)—C(223) | 110.6(7) |
| O(224)—C(224)—C(225) | 107.0(7) |
| C(223)—C(224)—C(225) | 113.7(7) |
| O(224)—C(224)—H(22B) | 108.4 |
| C(223)—C(224)—H(22B) | 108.5 |
| C(225)—C(224)—H(22B) | 108.5 |
| C(205)—C(204)—C(203) | 111.2(6) |
| C(205)—C(204)—H(20F) | 109.4 |
| C(203)—C(204)—H(20F) | 109.3 |
| C(205)—C(204)—H(20G) | 109.4 |
| C(203)—C(204)—H(20G) | 109.4 |
| H(20F)—C(204)—H(20G) | 108.0 |
| C(320)—C(317)—C(316) | 112.0(5) |
| C(320)—C(317)—C(313) | 120.2(5) |
| C(316)—C(317)—C(313) | 103.3(5) |
| C(320)—C(317)—H(31M) | 106.8 |
| C(316)—C(317)—H(31M) | 106.8 |
| C(313)—C(317)—H(31M) | 106.8 |
| C(206)—C(205)—C(204) | 121.3(7) |
| C(206)—C(205)—C(210) | 125.9(7) |
| C(204)—C(205)—C(210) | 112.7(6) |
| C(224)—O(224)—H(22C) | 109.5 |
| C(320)—C(321)—H(32G) | 109.5 |
| C(320)—C(321)—H(32H) | 109.5 |
| H(32G)—C(321)—H(32H) | 109.5 |
| C(320)—C(321)—H(32I) | 109.5 |
| H(32G)—C(321)—H(32I) | 109.5 |
| H(32H)—C(321)—H(32I) | 109.5 |
| C(219)—C(202)—C(201) | 123.2(7) |
| C(219)—C(202)—C(203) | 121.7(7) |
| C(201)—C(202)—C(203) | 115.1(6) |
| C(220)—C(221)—H(22D) | 109.5 |
| C(220)—C(221)—H(22E) | 109.4 |
| H(22D)—C(221)—H(22E) | 109.5 |
| C(220)—C(221)—H(22F) | 109.5 |
| H(22D)—C(221)—H(22F) | 109.5 |
| H(22E)—C(221)—H(22F) | 109.5 |
| C(223)—C(222)—C(220) | 127.9(7) |
| C(223)—C(222)—H(22G) | 116.1 |
| C(220)—C(222)—H(22G) | 116.0 |
| C(212)—C(211)—C(209) | 112.8(6) |
| C(212)—C(211)—H(21H) | 109.0 |
| C(209)—C(211)—H(21H) | 109.0 |
| C(212)—C(211)—H(21I) | 109.0 |
| C(209)—C(211)—H(21I) | 109.0 |
| H(21H)—C(211)—H(21I) | 107.8 |
| C(215)—C(216)—C(217) | 107.9(5) |
| C(215)—C(216)—H(21J) | 110.2 |
| C(217)—C(216)—H(21J) | 110.1 |
| C(215)—C(216)—H(21K) | 110.1 |
| C(217)—C(216)—H(21K) | 110.1 |
| H(21J)—C(216)—H(21K) | 108.4 |
| O(203)—C(203)—C(202) | 111.1(6) |
| O(203)—C(203)—C(204) | 107.2(6) |
| C(202)—C(203)—C(204) | 110.3(6) |
| O(203)—C(203)—H(20H) | 109.4 |
| C(202)—C(203)—H(20H) | 109.4 |
| C(204)—C(203)—H(20H) | 109.4 |
| C(314)—C(315)—C(316) | 104.7(5) |
| C(314)—C(315)—H(31N) | 110.8 |
| C(316)—C(315)—H(31N) | 110.8 |
| C(314)—C(315)—H(31O) | 110.8 |
| C(316)—C(315)—H(31O) | 110.8 |
| H(31N)—C(315)—H(31O) | 108.9 |
| C(125)—O(125)—H(12C) | 109.5 |
| C(122)—C(123)—C(124) | 125.1(7) |
| C(122)—C(123)—H(12D) | 117.5 |
| C(124)—C(123)—H(12D) | 117.4 |
| C(208)—C(209)—C(211) | 112.4(6) |
| C(208)—C(209)—H(20I) | 109.1 |
| C(211)—C(209)—H(20I) | 109.1 |
| C(208)—C(209)—H(20J) | 109.1 |
| C(211)—C(209)—H(20J) | 109.1 |
| H(20I)—C(209)—H(20J) | 107.9 |
| C(202)—C(219)—H(21L) | 120.0 |
| C(202)—C(219)—H(21M) | 120.0 |
| H(21L)—C(219)—H(21M) | 120.0 |
| C(222)—C(223)—C(224) | 122.8(7) |
| C(222)—C(223)—H(22H) | 118.6 |
| C(224)—C(223)—H(22H) | 118.6 |
| C(222)—C(220)—C(221) | 110.2(6) |
| C(222)—C(220)—C(217) | 107.5(6) |
| C(221)—C(220)—C(217) | 114.2(6) |
| C(222)—C(220)—H(22I) | 108.2 |
| C(221)—C(220)—H(22I) | 108.3 |
| C(217)—C(220)—H(22I) | 108.2 |
| C(114)—C(113)—C(118) | 111.5(6) |
| C(114)—C(113)—C(112) | 107.6(7) |
| C(118)—C(113)—C(112) | 111.0(7) |
| C(114)—C(113)—C(117) | 100.8(6) |
| C(118)—C(113)—C(117) | 109.8(6) |
| C(112)—C(113)—C(117) | 115.6(6) |
| C(302)—C(319)—H(31P) | 120.0 |
| C(302)—C(319)—H(31Q) | 120.0 |
| H(31P)—C(319)—H(31Q) | 120.0 |
| C(213)—C(212)—C(211) | 111.7(6) |
| C(213)—C(212)—H(21O) | 109.3 |
| C(211)—C(212)—H(21O) | 109.3 |
| C(213)—C(212)—H(21P) | 109.3 |
| C(211)—C(212)—H(21P) | 109.3 |
| H(21O)—C(212)—H(21P) | 107.9 |
| O(124)—C(124)—C(123) | 109.7(6) |
| O(124)—C(124)—C(125) | 109.7(6) |
| C(123)—C(124)—C(125) | 114.3(7) |
| O(124)—C(124)—H(12E) | 107.6 |
| C(123)—C(124)—H(12E) | 107.6 |
| C(125)—C(124)—H(12E) | 107.6 |
| C(111)—C(109)—C(108) | 113.9(8) |
| C(111)—C(109)—H(10A) | 108.8 |
| C(108)—C(109)—H(10A) | 108.8 |
| C(111)—C(109)—H(10B) | 108.8 |
| C(108)—C(109)—H(10B) | 108.8 |
| H(10A)—C(109)—H(10B) | 107.7 |
| C(113)—C(118)—H(11C) | 109.4 |
| C(113)—C(118)—H(11D) | 109.5 |
| H(11C)—C(118)—H(11D) | 109.5 |
| C(113)—C(118)—H(11E) | 109.5 |
| H(11C)—C(118)—H(11E) | 109.5 |
| H(11D)—C(118)—H(11E) | 109.5 |
| C(205)—C(210)—C(201) | 110.2(6) |
| C(205)—C(210)—H(21Q) | 109.6 |
| C(201)—C(210)—H(21Q) | 109.6 |
| C(205)—C(210)—H(21R) | 109.7 |
| C(201)—C(210)—H(21R) | 109.5 |
| H(21Q)—C(210)—H(21R) | 108.1 |

TABLE 3-continued

Bond lengths [Å] and angles [°].

| | |
|---|---|
| C(122)—C(120)—C(117) | 110.0(6) |
| C(122)—C(120)—C(121) | 108.1(6) |
| C(117)—C(120)—C(121) | 113.4(7) |
| C(122)—C(120)—H(12F) | 108.4 |
| C(117)—C(120)—H(12F) | 108.4 |
| C(121)—C(120)—H(12F) | 108.4 |
| O(325)—C(325)—C(326) | 109.2(8) |
| O(325)—C(325)—C(324) | 105.3(5) |
| C(326)—C(325)—C(324) | 114.7(8) |
| O(325)—C(325)—C(327) | 105.7(7) |
| C(326)—C(325)—C(327) | 113.5(11) |
| C(324)—C(325)—C(327) | 107.7(7) |
| C(120)—C(117)—C(113) | 120.7(6) |
| C(120)—C(117)—C(116) | 111.2(6) |
| C(113)—C(117)—C(116) | 103.4(6) |
| C(120)—C(117)—H(11F) | 106.9 |
| C(113)—C(117)—H(11F) | 106.9 |
| C(116)—C(117)—H(11F) | 107.0 |
| C(108)—C(114)—C(113) | 114.7(7) |
| C(108)—C(114)—C(115) | 119.5(7) |
| C(113)—C(114)—C(115) | 103.6(6) |
| C(108)—C(114)—H(11G) | 106.0 |
| C(113)—C(114)—H(11G) | 106.0 |
| C(115)—C(114)—H(11G) | 106.0 |
| O(125)—C(125)—C(127) | 109.2(8) |
| O(125)—C(125)—C(126) | 107.4(7) |
| C(127)—C(125)—C(126) | 110.0(8) |
| O(125)—C(125)—C(124) | 108.7(7) |
| C(127)—C(125)—C(124) | 111.0(7) |
| C(126)—C(125)—C(124) | 110.5(7) |
| C(114)—C(115)—C(116) | 102.7(7) |
| C(114)—C(115)—H(11H) | 111.2 |
| C(116)—C(115)—H(11H) | 111.3 |
| C(114)—C(115)—H(11I) | 111.2 |
| C(116)—C(115)—H(11I) | 111.2 |
| H(11H)—C(115)—H(11I) | 109.2 |
| C(111)—C(112)—C(113) | 110.6(8) |
| C(111)—C(112)—H(11J) | 109.5 |
| C(113)—C(112)—H(11J) | 109.5 |
| C(111)—C(112)—H(11K) | 109.5 |
| C(113)—C(112)—H(11K) | 109.5 |
| H(11J)—C(112)—H(11K) | 108.1 |
| C(107)—C(108)—C(114) | 125.1(8) |
| C(107)—C(108)—C(109) | 125.9(8) |
| C(114)—C(108)—C(109) | 109.1(8) |
| C(325)—C(327)—H(32J) | 109.5 |
| C(325)—C(327)—H(32K) | 109.4 |
| H(32J)—C(327)—H(32K) | 109.5 |
| C(325)—C(327)—H(32L) | 109.5 |
| H(32J)—C(327)—H(32L) | 109.5 |
| H(32K)—C(327)—H(32L) | 109.5 |
| O(225)—C(225)—C(224) | 104.8(8) |
| O(225)—C(225)—C(226) | 107.9(8) |
| C(224)—C(225)—C(226) | 110.8(8) |
| O(225)—C(225)—C(227) | 108.2(8) |
| C(224)—C(225)—C(227) | 110.4(8) |
| C(226)—C(225)—C(227) | 114.3(11) |
| C(120)—C(121)—H(12G) | 109.5 |
| C(120)—C(121)—H(12H) | 109.5 |
| H(12G)—C(121)—H(12H) | 109.5 |
| C(120)—C(121)—H(12I) | 109.5 |
| H(12G)—C(121)—H(12I) | 109.5 |
| H(12H)—C(121)—H(12I) | 109.5 |
| C(325)—C(326)—H(32M) | 109.5 |
| C(325)—C(326)—H(32N) | 109.4 |
| H(32M)—C(326)—H(32N) | 109.5 |
| C(325)—C(326)—H(32O) | 109.5 |
| H(32M)—C(326)—H(32O) | 109.5 |
| H(32N)—C(326)—H(32O) | 109.5 |
| C(105)—C(110)—C(101) | 112.0(11) |
| C(105)—C(110)—H(11L) | 109.2 |
| C(101)—C(110)—H(11L) | 109.3 |
| C(105)—C(110)—H(11M) | 109.1 |
| C(101)—C(110)—H(11M) | 109.2 |
| H(11L)—C(110)—H(11M) | 107.9 |
| C(105)—C(106)—C(107) | 129.9(11) |
| C(105)—C(106)—H(10C) | 115.0 |
| C(107)—C(106)—H(10C) | 115.0 |
| C(106)—C(105)—C(110) | 126.2(10) |
| C(106)—C(105)—C(104) | 120.5(12) |
| C(110)—C(105)—C(104) | 113.3(10) |
| C(125)—C(126)—H(12J) | 109.4 |
| C(125)—C(126)—H(12K) | 109.5 |
| H(12J)—C(126)—H(12K) | 109.5 |
| C(125)—C(126)—H(12L) | 109.6 |
| H(12J)—C(126)—H(12L) | 109.5 |
| H(12K)—C(126)—H(12L) | 109.5 |
| C(108)—C(107)—C(106) | 126.7(10) |
| C(108)—C(107)—H(10D) | 116.6 |
| C(106)—C(107)—H(10D) | 116.6 |
| C(225)—C(227)—H(22J) | 109.5 |
| C(225)—C(227)—H(22K) | 109.4 |
| H(22J)—C(227)—H(22K) | 109.5 |
| C(225)—C(227)—H(22L) | 109.6 |
| H(22J)—C(227)—H(22L) | 109.5 |
| H(22K)—C(227)—H(22L) | 109.5 |
| C(125)—C(127)—H(12M) | 109.4 |
| C(125)—C(127)—H(12N) | 109.5 |
| H(12M)—C(127)—H(12N) | 109.5 |
| C(125)—C(127)—H(12O) | 109.5 |
| H(12M)—C(127)—H(12O) | 109.5 |
| H(12N)—C(127)—H(12O) | 109.5 |
| C(225)—C(226)—H(22M) | 109.5 |
| C(225)—C(226)—H(22N) | 109.6 |
| H(22M)—C(226)—H(22N) | 109.5 |
| C(225)—C(226)—H(22O) | 109.3 |
| H(22M)—C(226)—H(22O) | 109.5 |
| H(22N)—C(226)—H(22O) | 109.5 |
| C(119)—C(102)—C(103) | 122.4(12) |
| C(119)—C(102)—C(101) | 125.2(15) |
| C(103)—C(102)—C(101) | 112.3(13) |
| C(109)—C(111)—C(112) | 113.4(9) |
| C(109)—C(111)—H(11N) | 108.9 |
| C(112)—C(111)—H(11N) | 108.9 |
| C(109)—C(111)—H(11O) | 108.9 |
| C(112)—C(111)—H(11O) | 108.9 |
| H(11N)—C(111)—H(11O) | 107.7 |
| C(102)—C(119)—H(11P) | 120.1 |
| C(102)—C(119)—H(11Q) | 119.9 |
| H(11P)—C(119)—H(11Q) | 120.0 |
| O(103)—C(103)—C(104) | 105.7(14) |
| O(103)—C(103)—C(102) | 116(2) |
| C(104)—C(103)—C(102) | 114.5(10) |
| O(103)—C(103)—H(10E) | 106.8 |
| C(104)—C(103)—H(10E) | 106.7 |
| C(102)—C(103)—H(10E) | 106.8 |
| C(101)—O(101)—H(10J) | 109.6 |
| C(105)—C(104)—C(103) | 106.8(14) |
| C(105)—C(104)—H(10F) | 110.2 |
| C(103)—C(104)—H(10F) | 110.2 |
| C(105)—C(104)—H(10G) | 110.6 |
| C(103)—C(104)—H(10G) | 110.6 |
| H(10F)—C(104)—H(10G) | 108.6 |
| O(101)—C(101)—C(102) | 109.5(13) |
| O(101)—C(101)—C(110) | 103.3(18) |
| C(102)—C(101)—C(110) | 107.2(12) |
| O(101)—C(101)—H(10H) | 112.0 |
| C(102)—C(101)—H(10H) | 112.2 |
| C(110)—C(101)—H(10H) | 112.2 |
| C(103)—O(103)—H(10I) | 109.4 |

TABLE 4

Anisotropic displacement parameters (Å$^2$ × 10$^3$). The anisotropic displacement factor exponent takes the form: $-2\pi^2 [h^2 a^{*2} U_{11} + \ldots + 2hka^*b^* U_{12}]$

| | U11 | U22 | U33 | U23 | U13 | U12 |
|---|---|---|---|---|---|---|
| O(301) | 42(2) | 32(2) | 82(3) | 4(2) | 32(2) | 0(2) |
| O(303) | 39(2) | 44(2) | 60(3) | 0(2) | 22(2) | 3(2) |
| O(325) | 58(3) | 48(3) | 69(3) | −14(2) | 41(2) | −5(2) |
| O(203) | 55(3) | 47(3) | 77(3) | −5(2) | 34(2) | −2(2) |
| C(313) | 29(3) | 41(3) | 51(3) | −3(3) | 23(3) | −4(3) |
| O(124) | 83(4) | 44(3) | 115(5) | −2(3) | 70(3) | 2(3) |
| C(304) | 37(3) | 41(3) | 61(4) | −1(3) | 27(3) | −2(3) |
| O(201) | 75(3) | 50(3) | 77(3) | −11(3) | 30(3) | −1(3) |
| C(307) | 31(3) | 32(3) | 62(4) | −3(3) | 24(3) | −1(2) |
| O(324) | 41(2) | 102(4) | 92(4) | −49(3) | 37(3) | −17(3) |
| C(308) | 29(3) | 41(3) | 58(4) | −3(3) | 24(3) | −2(2) |
| C(301) | 35(3) | 41(3) | 55(4) | 4(3) | 26(3) | −1(3) |
| C(314) | 40(3) | 41(3) | 59(4) | −6(3) | 29(3) | −5(3) |
| C(305) | 36(3) | 46(4) | 53(4) | −5(3) | 22(3) | −2(3) |
| C(208) | 45(3) | 52(4) | 48(4) | 7(3) | 22(3) | 7(3) |
| C(322) | 38(3) | 40(3) | 63(4) | −2(3) | 32(3) | −6(3) |
| O(225) | 99(5) | 119(6) | 82(4) | 19(4) | 54(4) | 25(4) |
| C(318) | 37(3) | 44(3) | 56(4) | 2(3) | 26(3) | 1(3) |
| C(206) | 51(4) | 49(4) | 51(4) | 2(3) | 21(3) | 2(3) |
| C(323) | 39(3) | 38(3) | 62(4) | −8(3) | 30(3) | −8(3) |
| C(302) | 33(3) | 46(4) | 50(4) | 0(3) | 22(3) | −6(3) |
| C(201) | 58(4) | 40(3) | 74(5) | −3(3) | 33(4) | 1(3) |
| C(324) | 38(3) | 51(4) | 56(4) | −6(3) | 27(3) | 5(3) |
| C(306) | 32(3) | 38(3) | 61(4) | 0(3) | 22(3) | −1(3) |
| C(207) | 48(3) | 47(4) | 52(4) | 0(3) | 21(3) | 5(3) |
| C(309) | 39(3) | 50(4) | 67(4) | 10(3) | 30(3) | 6(3) |
| C(311) | 41(3) | 38(3) | 71(4) | 2(3) | 31(3) | 3(3) |
| C(214) | 45(3) | 42(3) | 53(4) | 2(3) | 20(3) | 3(3) |
| C(303) | 40(3) | 45(3) | 49(4) | −3(3) | 26(3) | −1(3) |
| C(312) | 42(3) | 41(3) | 63(4) | 5(3) | 32(3) | 1(3) |
| C(320) | 38(3) | 46(4) | 54(4) | −4(3) | 28(3) | −1(3) |
| C(116) | 51(4) | 58(4) | 76(5) | −8(4) | 32(4) | −2(3) |
| C(213) | 45(3) | 43(4) | 59(4) | 0(3) | 25(3) | −2(3) |
| C(217) | 47(3) | 44(3) | 58(4) | 1(3) | 27(3) | −1(3) |
| C(122) | 75(5) | 49(4) | 63(5) | 6(3) | 34(4) | 9(4) |
| C(310) | 35(3) | 45(4) | 62(4) | 5(3) | 25(3) | −2(3) |
| C(218) | 48(4) | 46(4) | 63(4) | 6(3) | 17(3) | −1(3) |
| C(215) | 45(3) | 55(4) | 59(4) | −4(3) | 24(3) | −1(3) |
| C(316) | 48(4) | 48(4) | 80(5) | −13(4) | 45(3) | −8(3) |
| C(224) | 57(4) | 69(5) | 74(5) | 5(4) | 30(4) | 14(4) |
| C(204) | 59(4) | 59(4) | 61(5) | −3(4) | 26(4) | −16(4) |
| C(317) | 36(3) | 40(3) | 53(4) | −8(3) | 26(3) | −3(3) |
| C(205) | 55(4) | 48(4) | 60(4) | 0(3) | 23(3) | 4(3) |
| O(224) | 71(4) | 126(6) | 92(4) | 6(4) | 45(3) | 16(4) |
| C(321) | 50(4) | 42(4) | 80(5) | −10(3) | 40(4) | −6(3) |
| C(202) | 52(4) | 44(4) | 59(4) | 5(3) | 21(3) | −3(3) |
| C(221) | 48(4) | 72(5) | 81(5) | −7(4) | 29(4) | −5(4) |
| C(222) | 48(4) | 49(4) | 76(5) | −6(4) | 27(3) | −1(3) |
| C(211) | 60(4) | 54(4) | 56(4) | −3(3) | 25(3) | −10(3) |
| C(216) | 48(3) | 59(4) | 59(4) | 4(3) | 29(3) | 4(3) |
| C(203) | 53(4) | 51(4) | 69(5) | −5(4) | 29(4) | −8(3) |
| C(315) | 57(4) | 38(4) | 92(5) | −12(3) | 52(4) | −8(3) |
| O(125) | 71(4) | 110(5) | 85(4) | 14(4) | 33(3) | −13(4) |
| C(123) | 63(4) | 50(4) | 70(5) | 9(4) | 37(4) | 9(4) |
| C(209) | 50(4) | 47(4) | 61(4) | 2(3) | 28(3) | 2(3) |
| C(219) | 55(4) | 58(4) | 72(5) | −7(4) | 21(4) | −10(4) |
| C(223) | 56(4) | 52(4) | 72(5) | −4(4) | 34(4) | −2(3) |
| C(220) | 48(4) | 46(4) | 71(5) | −4(3) | 30(3) | −3(3) |
| C(113) | 70(4) | 49(4) | 61(4) | 3(4) | 23(4) | −7(4) |
| C(319) | 50(4) | 57(4) | 65(4) | 11(4) | 34(3) | 4(3) |
| C(212) | 49(4) | 50(4) | 60(4) | −4(3) | 23(3) | −1(3) |
| C(124) | 61(4) | 46(4) | 79(5) | 7(3) | 40(4) | 8(3) |
| C(109) | 63(5) | 99(7) | 89(6) | 6(6) | 25(5) | −19(5) |
| C(118) | 77(5) | 47(4) | 80(5) | 1(4) | 31(4) | −9(4) |
| C(210) | 50(4) | 48(4) | 79(5) | −3(4) | 26(4) | 0(3) |
| C(120) | 71(5) | 50(4) | 66(5) | 8(4) | 31(4) | 2(4) |
| C(325) | 76(5) | 48(4) | 86(5) | −13(4) | 60(4) | −11(4) |
| C(117) | 59(4) | 45(4) | 66(4) | 11(3) | 25(3) | −2(3) |
| C(114) | 55(4) | 57(4) | 76(5) | 11(4) | 26(4) | −1(4) |
| C(125) | 83(5) | 64(5) | 68(5) | 2(4) | 41(4) | 0(4) |
| C(115) | 62(5) | 64(5) | 90(6) | −12(4) | 31(4) | −11(4) |
| C(112) | 76(5) | 65(5) | 78(6) | 17(4) | 18(4) | −13(4) |
| C(108) | 55(4) | 71(5) | 87(6) | 12(5) | 21(4) | −8(4) |
| C(327) | 64(5) | 96(7) | 123(8) | −50(6) | 40(5) | −24(5) |
| C(225) | 90(6) | 89(7) | 76(6) | 14(5) | 46(5) | 19(5) |

TABLE 4-continued

Anisotropic displacement parameters ($Å^2 \times 10^3$). The anisotropic displacement factor exponent takes the form: $-2\pi^2 [h^2 a^{*2} U_{11} + \ldots + 2hka^*b^*U_{12}]$

|  | U11 | U22 | U33 | U23 | U13 | U12 |
|---|---|---|---|---|---|---|
| C(121) | 86(6) | 66(5) | 83(6) | 0(5) | 38(5) | −6(5) |
| C(326) | 390(30) | 47(5) | 125(10) | −17(6) | 176(15) | −8(9) |
| C(110) | 67(5) | 115(8) | 117(8) | 8(7) | 46(6) | −17(6) |
| C(106) | 82(7) | 130(10) | 122(10) | −23(8) | 33(7) | −43(7) |
| C(105) | 81(6) | 109(8) | 86(7) | 6(6) | 44(5) | −11(6) |
| C(126) | 100(7) | 82(6) | 99(7) | −29(6) | 51(6) | 0(6) |
| C(107) | 64(5) | 78(6) | 98(7) | 3(5) | 40(5) | −13(4) |
| C(227) | 156(11) | 98(8) | 75(7) | −22(6) | 41(7) | −17(6) |
| C(127) | 137(9) | 68(6) | 113(8) | −14(5) | 75(7) | −33(6) |
| C(226) | 81(6) | 172(13) | 87(7) | 3(7) | 38(6) | 35(8) |
| C(102) | 79(6) | 101(8) | 132(10) | 52(7) | 46(7) | 17(6) |
| C(111) | 90(7) | 103(8) | 80(6) | 12(6) | −7(5) | −41(6) |
| C(119) | 94(8) | 95(8) | 151(12) | 31(8) | 59(8) | 7(6) |
| C(103) | 56(6) | 370(30) | 98(9) | 59(15) | 37(6) | −12(12) |
| O(101) | 530(40) | 430(30) | 520(30) | −380(30) | 460(30) | −380(30) |
| C(104) | 123(10) | 195(16) | 122(10) | −25(10) | 71(9) | −76(11) |
| C(101) | 150(13) | 134(12) | 229(19) | −24(13) | 149(14) | −14(10) |
| O(103) | 107(7) | 840(60) | 131(9) | 200(19) | 70(7) | 168(17) |
| O(2) | 300(30) | 990(120) | 400(50) | −240(70) | −180(40) | −70(50) |
| O(1) | 153(8) | 198(11) | 101(6) | −15(6) | 63(6) | 33(8) |
| O(3) | 350(50) | 2000(300) | 460(60) | −400(120) | 300(50) | −400(110) |
| O(4) | 500(60) | 2000(300) | 210(20) | 480(80) | −140(30) | −160(110) |

TABLE 5

Hydrogen coordinates ($Å \times 10^4$) and isotropic displacement parameters ($Å^2 \times 10^3$).

|  | x | y | z | U(eq) |
|---|---|---|---|---|
| H(30A) | 6176 | 2121 | 325 | 73 |
| H(30B) | 4245 | 6222 | −201 | 69 |
| H(32A) | 11486 | 4676 | −2293 | 80 |
| H(20A) | 10549 | 12997 | −2770 | 85 |
| H(12A) | 11774 | 6665 | −2750 | 107 |
| H(30C) | 5436 | 7553 | 489 | 53 |
| H(30D) | 5985 | 6717 | 1011 | 53 |
| H(20B) | 11722 | 8900 | −3254 | 99 |
| H(30E) | 7615 | 6690 | −159 | 47 |
| H(32B) | 12682 | 7487 | −1182 | 112 |
| H(30F) | 5822 | 4048 | −93 | 49 |
| H(31A) | 7833 | 8669 | −1092 | 53 |
| H(32C) | 10358 | 9105 | −1690 | 52 |
| H(22A) | 18172 | 13343 | −4632 | 141 |
| H(31B) | 9800 | 8250 | 51 | 65 |
| H(31C) | 10060 | 9792 | 117 | 65 |
| H(31D) | 9257 | 9266 | 287 | 65 |
| H(20C) | 13271 | 13226 | −1743 | 59 |
| H(32D) | 11581 | 7724 | −875 | 52 |
| H(20D) | 11669 | 11530 | −3200 | 66 |
| H(32E) | 11321 | 7887 | −2018 | 55 |
| H(30G) | 6429 | 8359 | 142 | 50 |
| H(20E) | 14031 | 12311 | −2525 | 57 |
| H(30H) | 6938 | 10034 | −130 | 59 |
| H(30I) | 6837 | 10129 | −761 | 59 |
| H(31E) | 7719 | 11904 | −335 | 56 |
| H(31F) | 8326 | 10956 | 127 | 56 |
| H(21A) | 15329 | 14837 | −2412 | 55 |
| H(30J) | 4622 | 5693 | 656 | 50 |
| H(31G) | 8285 | 11030 | −984 | 54 |
| H(31H) | 9085 | 11481 | −470 | 54 |
| H(32F) | 10733 | 9154 | −530 | 51 |
| H(11A) | 14998 | 5863 | −3433 | 71 |
| H(11B) | 14640 | 7225 | −3751 | 71 |
| H(21B) | 16826 | 14943 | −2362 | 57 |
| H(12B) | 14256 | 6735 | −2530 | 71 |
| H(31I) | 7203 | 5010 | 822 | 54 |
| H(31J) | 7187 | 5016 | 205 | 54 |
| H(21C) | 16353 | 11655 | −2001 | 78 |
| H(21D) | 17046 | 12167 | −1447 | 78 |
| H(21E) | 16042 | 12066 | −1500 | 78 |
| H(21F) | 14882 | 13442 | −3125 | 62 |
| H(21G) | 15237 | 12143 | −2756 | 62 |
| H(31K) | 9194 | 7144 | −1361 | 64 |
| H(31L) | 9887 | 7054 | −760 | 64 |
| H(22B) | 18593 | 14635 | −3398 | 78 |
| H(20F) | 12101 | 12250 | −1617 | 70 |
| H(20G) | 12091 | 10667 | −1692 | 70 |
| H(31M) | 9046 | 9350 | −1328 | 48 |
| H(22C) | 19861 | 13609 | −3036 | 138 |
| H(32G) | 10238 | 11397 | −635 | 79 |
| H(32H) | 11040 | 11220 | −855 | 79 |
| H(32I) | 10074 | 11307 | −1274 | 79 |
| H(22D) | 18173 | 13754 | −1333 | 98 |
| H(22E) | 18970 | 13676 | −1563 | 98 |
| H(22F) | 18397 | 15002 | −1646 | 98 |
| H(22G) | 18062 | 14821 | −2699 | 67 |
| H(21H) | 15853 | 15294 | −885 | 66 |
| H(21I) | 15857 | 13714 | −961 | 66 |
| H(21J) | 16213 | 13940 | −3151 | 63 |
| H(21K) | 16503 | 12479 | −2909 | 63 |
| H(20H) | 10683 | 11442 | −2125 | 66 |
| H(31N) | 8176 | 6510 | −1004 | 67 |
| H(31O) | 8835 | 6690 | −395 | 67 |
| H(12C) | 12249 | 6619 | −4146 | 130 |
| H(12D) | 13100 | 7957 | −3423 | 69 |
| H(20I) | 14418 | 14390 | −1361 | 60 |
| H(20J) | 14692 | 15561 | −1689 | 60 |
| H(21L) | 10346 | 9104 | −3160 | 93 |
| H(21M) | 9965 | 9750 | −2703 | 93 |
| H(22H) | 18508 | 12210 | −2828 | 68 |
| H(22I) | 17797 | 12496 | −2138 | 63 |
| H(31P) | 4865 | 3604 | 1087 | 80 |
| H(31Q) | 5594 | 2569 | 1005 | 80 |
| H(21O) | 16427 | 15630 | −1592 | 62 |
| H(21P) | 17039 | 14587 | −1176 | 62 |
| H(12E) | 12901 | 5800 | −2760 | 70 |
| H(10A) | 18388 | 7351 | −2666 | 100 |
| H(10B) | 18660 | 8528 | −2990 | 100 |
| H(11C) | 15758 | 10201 | −3197 | 100 |
| H(11D) | 16491 | 9929 | −3470 | 100 |
| H(11E) | 15551 | 9271 | −3723 | 100 |
| H(21Q) | 12741 | 9706 | −2416 | 69 |
| H(21R) | 13079 | 10761 | −2763 | 69 |

TABLE 5-continued

Hydrogen coordinates (Å × 10⁴) and isotropic displacement parameters (Å² × 10³).

| | x | y | z | U(eq) |
|---|---|---|---|---|
| H(12F) | 14524 | 8977 | −3133 | 72 |
| H(11F) | 15745 | 6896 | −2665 | 67 |
| H(11G) | 16871 | 6501 | −3032 | 74 |
| H(11H) | 15990 | 5824 | −3870 | 84 |
| H(11I) | 15759 | 7329 | −4083 | 84 |
| H(11J) | 16801 | 9437 | −2305 | 89 |
| H(11K) | 17143 | 7931 | −2232 | 89 |
| H(32J) | 9908 | 6342 | −1943 | 138 |
| H(32K) | 10168 | 6622 | −2475 | 138 |
| H(32L) | 10033 | 5125 | −2307 | 138 |
| H(12G) | 15550 | 9726 | −2294 | 114 |
| H(12H) | 14605 | 9584 | −2239 | 114 |
| H(12I) | 15324 | 8466 | −1989 | 114 |
| H(32M) | 11108 | 5369 | −1107 | 250 |
| H(32N) | 11194 | 4146 | −1479 | 250 |
| H(32O) | 12031 | 5007 | −1163 | 250 |
| H(11L) | 17781 | 7726 | −5286 | 115 |
| H(11M) | 17564 | 6696 | −4879 | 115 |
| H(10C) | 18730 | 8635 | −3772 | 134 |
| H(12J) | 13278 | 4095 | −3364 | 134 |
| H(12K) | 12757 | 4080 | −4001 | 134 |
| H(12L) | 13413 | 5271 | −3743 | 134 |
| H(10D) | 17120 | 7265 | −4191 | 92 |
| H(22J) | 17851 | 11224 | −3670 | 163 |
| H(22K) | 17803 | 11227 | −4294 | 163 |
| H(22L) | 18724 | 11272 | −3824 | 163 |
| H(12M) | 11870 | 3937 | −3176 | 146 |
| H(12N) | 11118 | 4989 | −3451 | 146 |
| H(12O) | 11383 | 3901 | −3818 | 146 |
| H(22M) | 16896 | 13354 | −3835 | 166 |
| H(22N) | 17213 | 14637 | −4082 | 166 |
| H(22O) | 16845 | 13368 | −4459 | 166 |
| H(11N) | 17725 | 9989 | −2791 | 119 |
| H(11O) | 18295 | 9307 | −2234 | 119 |
| H(11P) | 20148 | 7348 | −5603 | 162 |
| H(11Q) | 19417 | 6187 | −5860 | 162 |
| H(10E) | 20268 | 8376 | −4813 | 206 |
| H(10J) | 18421 | 4963 | −5709 | 638 |
| H(10F) | 19496 | 9369 | −4271 | 167 |
| H(10G) | 18961 | 9424 | −4910 | 167 |
| H(10H) | 18859 | 5427 | −4794 | 180 |
| H(10I) | 20735 | 6854 | −4210 | 530 |

TABLE 6

Torsion angles [°].

| | |
|---|---|
| C(306)—C(307)—C(308)—C(309) | 1.2(11) |
| C(306)—C(307)—C(308)—C(314) | −172.7(6) |
| C(307)—C(308)—C(314)—C(315) | −5.4(10) |
| C(309)—C(308)—C(314)—C(315) | 179.9(6) |
| C(307)—C(308)—C(314)—C(313) | −130.1(6) |
| C(309)—C(308)—C(314)—C(313) | 55.3(7) |
| C(312)—C(313)—C(314)—C(315) | 169.1(6) |
| C(318)—C(313)—C(314)—C(315) | −68.2(8) |
| C(317)—C(313)—C(314)—C(315) | 47.2(6) |
| C(312)—C(313)—C(314)—C(308) | −57.6(7) |
| C(318)—C(313)—C(314)—C(308) | 65.1(7) |
| C(317)—C(313)—C(314)—C(308) | −179.5(5) |
| C(303)—C(304)—C(305)—C(306) | 134.1(6) |
| C(303)—C(304)—C(305)—C(310) | −48.6(8) |
| C(320)—C(322)—C(323)—C(324) | 178.5(6) |
| O(301)—C(301)—C(302)—C(319) | 0.1(9) |
| C(310)—C(301)—C(302)—C(319) | −123.7(7) |
| O(301)—C(301)—C(302)—C(303) | −178.4(5) |
| C(310)—C(301)—C(302)—C(303) | 57.8(7) |
| C(322)—C(323)—C(324)—O(324) | 134.3(6) |
| C(322)—C(323)—C(324)—C(325) | −102.8(8) |
| C(304)—C(305)—C(306)—C(307) | −177.2(6) |
| C(310)—C(305)—C(306)—C(307) | 5.8(11) |
| C(308)—C(307)—C(306)—C(305) | 179.8(7) |
| C(214)—C(208)—C(207)—C(206) | −178.5(6) |

TABLE 6-continued

Torsion angles [°].

| | |
|---|---|
| C(209)—C(208)—C(207)—C(206) | 1.4(11) |
| C(205)—C(206)—C(207)—C(208) | −171.5(7) |
| C(307)—C(308)—C(309)—C(311) | 135.4(7) |
| C(314)—C(308)—C(309)—C(311) | −50.2(8) |
| C(308)—C(309)—C(311)—C(312) | 50.3(8) |
| C(207)—C(208)—C(214)—C(215) | 2.2(10) |
| C(209)—C(208)—C(214)—C(215) | −177.7(6) |
| C(207)—C(208)—C(214)—C(213) | −124.7(7) |
| C(209)—C(208)—C(214)—C(213) | 55.4(7) |
| C(319)—C(302)—C(303)—O(303) | −116.4(7) |
| C(301)—C(302)—C(303)—O(303) | 62.1(6) |
| C(319)—C(302)—C(303)—C(304) | 122.0(7) |
| C(301)—C(302)—C(303)—C(304) | −59.5(7) |
| C(305)—C(304)—C(303)—O(303) | −64.5(8) |
| C(305)—C(304)—C(303)—C(302) | 54.4(7) |
| C(318)—C(313)—C(312)—C(311) | −67.7(7) |
| C(317)—C(313)—C(312)—C(311) | 165.7(5) |
| C(314)—C(313)—C(312)—C(311) | 55.2(7) |
| C(309)—C(311)—C(312)—C(313) | −53.4(8) |
| C(323)—C(322)—C(320)—C(321) | 121.7(7) |
| C(323)—C(322)—C(320)—C(317) | −114.2(7) |
| C(208)—C(214)—C(213)—C(212) | −58.0(7) |
| C(215)—C(214)—C(213)—C(212) | 167.2(6) |
| C(208)—C(214)—C(213)—C(218) | 64.5(8) |
| C(215)—C(214)—C(213)—C(218) | −70.3(7) |
| C(208)—C(214)—C(213)—C(217) | −179.5(6) |
| C(215)—C(214)—C(213)—C(217) | 45.7(6) |
| C(212)—C(213)—C(217)—C(216) | −151.8(6) |
| C(218)—C(213)—C(217)—C(216) | 79.8(6) |
| C(214)—C(213)—C(217)—C(216) | −36.1(6) |
| C(212)—C(213)—C(217)—C(220) | 82.9(6) |
| C(218)—C(213)—C(217)—C(220) | −45.5(8) |
| C(214)—C(213)—C(217)—C(220) | −161.4(6) |
| C(306)—C(305)—C(310)—C(301) | −136.2(7) |
| C(304)—C(305)—C(310)—C(301) | 46.6(8) |
| O(301)—C(301)—C(310)—C(305) | −175.3(5) |
| C(302)—C(301)—C(310)—C(305) | −49.9(7) |
| C(208)—C(214)—C(215)—C(216) | −167.4(6) |
| C(213)—C(214)—C(215)—C(216) | −36.2(7) |
| C(322)—C(320)—C(317)—C(316) | 53.9(7) |
| C(321)—C(320)—C(317)—C(316) | 175.7(6) |
| C(322)—C(320)—C(317)—C(313) | 175.5(5) |
| C(321)—C(320)—C(317)—C(313) | −62.7(8) |
| C(315)—C(316)—C(317)—C(320) | 150.4(6) |
| C(315)—C(316)—C(317)—C(313) | 19.6(7) |
| C(312)—C(313)—C(317)—C(320) | 78.8(7) |
| C(318)—C(313)—C(317)—C(320) | −48.5(7) |
| C(314)—C(313)—C(317)—C(320) | −165.4(6) |
| C(312)—C(313)—C(317)—C(316) | −155.4(6) |
| C(318)—C(313)—C(317)—C(316) | 77.3(6) |
| C(314)—C(313)—C(317)—C(316) | −39.6(6) |
| C(207)—C(206)—C(205)—C(204) | 179.1(7) |
| C(207)—C(206)—C(205)—C(210) | −3.3(12) |
| C(203)—C(204)—C(205)—C(206) | 120.9(7) |
| C(203)—C(204)—C(205)—C(210) | −57.0(8) |
| O(201)—C(201)—C(202)—C(219) | −1.9(10) |
| C(210)—C(201)—C(202)—C(219) | −127.0(8) |
| O(201)—C(201)—C(202)—C(203) | 177.3(6) |
| C(210)—C(201)—C(202)—C(203) | 52.2(8) |
| C(214)—C(215)—C(216)—C(217) | 12.7(7) |
| C(213)—C(217)—C(216)—C(215) | 15.3(7) |
| C(220)—C(217)—C(216)—C(215) | 146.5(6) |
| C(219)—C(202)—C(203)—O(203) | −115.1(8) |
| C(201)—C(202)—C(203)—O(203) | 65.7(8) |
| C(219)—C(202)—C(203)—C(204) | 126.1(8) |
| C(201)—C(202)—C(203)—C(204) | −53.1(8) |
| C(205)—C(204)—C(203)—O(203) | −67.2(8) |
| C(205)—C(204)—C(203)—C(202) | 53.9(8) |
| C(308)—C(314)—C(315)—C(316) | −164.8(6) |
| C(313)—C(314)—C(315)—C(316) | −35.7(7) |
| C(317)—C(316)—C(315)—C(314) | 9.9(8) |
| C(120)—C(122)—C(123)—C(124) | −179.3(7) |
| C(207)—C(208)—C(209)—C(211) | 130.6(7) |
| C(214)—C(208)—C(209)—C(211) | −49.5(8) |
| C(212)—C(211)—C(209)—C(208) | 49.5(8) |
| C(220)—C(222)—C(223)—C(224) | 175.5(7) |
| O(224)—C(224)—C(223)—C(222) | 125.8(8) |
| C(225)—C(224)—C(223)—C(222) | −113.7(9) |

TABLE 6-continued

| Torsion angles [°]. | |
|---|---|
| C(223)—C(222)—C(220)—C(221) | 112.0(8) |
| C(223)—C(222)—C(220)—C(217) | −122.9(8) |
| C(213)—C(217)—C(220)—C(222) | −179.2(6) |
| C(216)—C(217)—C(220)—C(222) | 59.0(7) |
| C(213)—C(217)—C(220)—C(221) | −56.6(9) |
| C(216)—C(217)—C(220)—C(221) | 178.4(6) |
| C(218)—C(213)—C(212)—C(211) | −65.7(8) |
| C(217)—C(213)—C(212)—C(211) | 166.8(6) |
| C(214)—C(213)—C(212)—C(211) | 55.6(7) |
| C(209)—C(211)—C(212)—C(213) | −53.7(8) |
| C(122)—C(123)—C(124)—O(124) | 118.6(8) |
| C(122)—C(123)—C(124)—C(125) | −117.7(9) |
| C(206)—C(205)—C(210)—C(201) | −122.8(8) |
| C(204)—C(205)—C(210)—C(201) | 54.9(8) |
| O(201)—C(201)—C(210)—C(205) | −177.8(6) |
| C(202)—C(201)—C(210)—C(205) | −51.2(8) |
| C(123)—C(122)—C(120)—C(117) | −115.6(9) |
| C(123)—C(122)—C(120)—C(121) | 120.0(9) |
| O(324)—C(324)—C(325)—O(325) | −49.3(8) |
| C(323)—C(324)—C(325)—O(325) | −171.4(6) |
| O(324)—C(324)—C(325)—C(326) | 70.8(11) |
| C(323)—C(324)—C(325)—C(326) | −51.3(12) |
| O(324)—C(324)—C(325)—C(327) | −161.7(7) |
| C(323)—C(324)—C(325)—C(327) | 76.2(8) |
| C(122)—C(120)—C(117)—C(113) | 178.5(7) |
| C(121)—C(120)—C(117)—C(113) | −60.3(9) |
| C(122)—C(120)—C(117)—C(116) | 57.2(8) |
| C(121)—C(120)—C(117)—C(116) | 178.4(6) |
| C(114)—C(113)—C(117)—C(120) | −164.4(7) |
| C(118)—C(113)—C(117)—C(120) | −46.7(9) |
| C(112)—C(113)—C(117)—C(120) | 79.9(9) |
| C(114)—C(113)—C(117)—C(116) | −39.4(7) |
| C(118)—C(113)—C(117)—C(116) | 78.3(7) |
| C(112)—C(113)—C(117)—C(116) | −155.1(7) |
| C(115)—C(116)—C(117)—C(120) | 148.5(7) |
| C(115)—C(116)—C(117)—C(113) | 17.5(8) |
| C(118)—C(113)—C(114)—C(108) | 63.2(9) |
| C(112)—C(113)—C(114)—C(108) | −58.8(8) |
| C(117)—C(113)—C(114)—C(108) | 179.7(7) |
| C(118)—C(113)—C(114)—C(115) | −68.8(8) |
| C(112)—C(113)—C(114)—C(115) | 169.2(6) |
| C(117)—C(113)—C(114)—C(115) | 47.7(7) |
| O(124)—C(124)—C(125)—O(125) | 63.8(8) |
| C(123)—C(124)—C(125)—O(125) | −59.9(9) |
| O(124)—C(124)—C(125)—C(127) | −56.3(9) |
| C(123)—C(124)—C(125)—C(127) | 180.0(8) |
| O(124)—C(124)—C(125)—C(126) | −178.6(7) |
| C(123)—C(124)—C(125)—C(126) | 57.7(9) |
| C(108)—C(114)—C(115)—C(116) | −165.5(7) |
| C(113)—C(114)—C(115)—C(116) | −36.4(8) |
| C(117)—C(116)—C(115)—C(114) | 11.3(8) |
| C(114)—C(113)—C(112)—C(111) | 55.2(10) |
| C(118)—C(113)—C(112)—C(111) | −67.0(8) |
| C(117)—C(113)—C(112)—C(111) | 167.0(8) |
| C(113)—C(114)—C(108)—C(107) | −124.0(10) |
| C(115)—C(114)—C(108)—C(107) | −0.1(13) |
| C(113)—C(114)—C(108)—C(109) | 56.0(10) |
| C(115)—C(114)—C(108)—C(109) | 179.8(8) |
| C(111)—C(109)—C(108)—C(107) | 129.2(11) |
| C(111)—C(109)—C(108)—C(114) | −50.8(11) |
| O(224)—C(224)—C(225)—O(225) | −50.2(9) |
| C(223)—C(224)—C(225)—O(225) | −172.6(7) |
| O(224)—C(224)—C(225)—C(226) | −166.3(9) |
| C(223)—C(224)—C(225)—C(226) | 71.3(11) |
| O(224)—C(224)—C(225)—C(227) | 66.1(10) |
| C(223)—C(224)—C(225)—C(227) | −56.3(10) |
| C(107)—C(106)—C(105)—C(110) | −9(2) |
| C(107)—C(106)—C(105)—C(104) | 168.6(14) |
| C(101)—C(110)—C(105)—C(106) | −120.2(15) |
| C(101)—C(110)—C(105)—C(104) | 61.6(15) |
| C(114)—C(108)—C(107)—C(106) | 174.8(10) |
| C(109)—C(108)—C(107)—C(106) | −5.2(18) |
| C(105)—C(106)—C(107)—C(108) | 171.5(4) |
| C(108)—C(109)—C(111)—C(112) | 51.9(12) |
| C(113)—C(112)—C(111)—C(109) | −53.9(11) |
| C(119)—C(102)—C(103)—O(103) | −114.4(13) |
| C(101)—C(102)—C(103)—O(103) | 68.6(15) |
| C(119)—C(102)—C(103)—C(104) | 122.2(13) |

TABLE 6-continued

| Torsion angles [°]. | |
|---|---|
| C(101)—C(102)—C(103)—C(104) | −54.8(18) |
| C(106)—C(105)—C(104)—C(103) | 123.0(14) |
| C(110)—C(105)—C(104)—C(103) | −58.7(15) |
| O(103)—C(103)—C(104)—C(105) | −73.2(19) |
| C(102)—C(103)—C(104)—C(105) | 55.4(16) |
| C(119)—C(102)—C(101)—O(101) | −15(2) |
| C(103)—C(102)—C(101)—O(101) | 162.2(19) |
| C(119)—C(102)—C(101)—C(110) | −126.2(14) |
| C(103)—C(102)—C(101)—C(110) | 50.7(19) |
| C(105)—C(110)—C(101)—O(101) | −170.0(13) |
| C(105)—C(110)—C(101)—C(102) | −54.4(17) |

Symmetry Transformations Used to Generate Equivalent Atoms:

We claim:

1. A compound having the formula

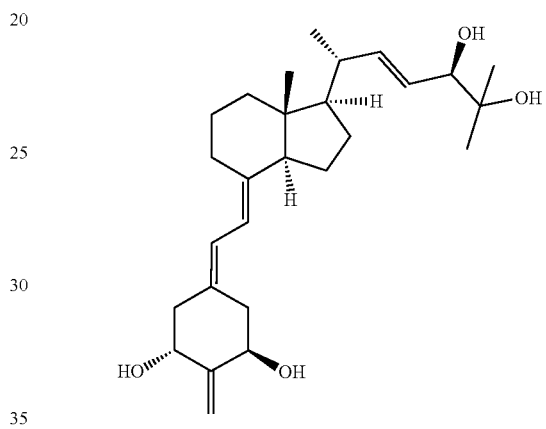

in a crystalline form and named (22E)-(24R)-2-methylene-22-dehydro-1α,24,25-trihydroxy-19-nor-vitamin D$_3$, wherein the crystalline form has molecular packing arrangement defined by space group P2$_1$ and unit cell dimensions: a=16.3058(9) Å; b=10.0461(6) Å; c=26.0527(15) Å; α=90°; β=109.001(3)°; and γ=90°.

2. A three dimensional structure for (22E)-(24R)-2-methylene-22-dehydro-1α,24,25-trihydroxy-19-nor-vitamin D$_3$ as defined by the molecular packing arrangement set forth in claim 1.

3. A method of purifying (22E)-(24R)-2-methylene-22-dehydro-1α,24,25-trihydroxy-19-nor-vitamin D$_3$, comprising the steps of:
   (a) dissolving (22E)-(24R)-2-methylene-22-dehydro-1α,24,25-trihydroxy-19-nor-vitamin D$_3$ in a volume of ethyl acetate as solvent to prepare a solution of (22E)-(24R)-2-methylene-22-dehydro-1α,24,25-trihydroxy-19-nor-vitamin D$_3$,
   (b) adding a volume of hexane dropwise to the solution, to reach a saturation point, to form a solution of (22E)-(24R)-2-methylene-22-dehydro -1α,24,25-trihydroxy-19-nor-vitamin D$_3$ in a mixture of ethyl acetate and hexane as solvent wherein crystals of (22E)-(24R)-2-methylene-22-dehydro-1α,24,25-trihydroxy-19-nor-vitamin D$_3$ form and precipitate from the solution; and
   (c) separating the (22E)-(24R)-2-methylene-22-dehydro-1α,24,25-trihydroxy-19-nor-vitamin D$_3$ crystals from the solution, wherein the (22E)-(24R)-2-methylene-22-dehydro-1α,24,25-trihydroxy-19-nor-vitamin D$_3$ crystals have a crystalline form that has molecular packing arrangement defined by space group P2$_1$ and unit cell dimensions: a=16.3058(9) Å; b=10.0461(6) Å; c=26.0527(15) Å; α=90°; β=109.001(3)°; and γ=90°.

4. The method of claim 3, wherein the solution of (22E)-(24R)-2-methylene-22-dehydro-α,24,25-trihydroxy-19-nor-vitamin $D_3$ in the mixture of ethyl acetate and hexane as solvent is placed at room temperature, wherein crystals of (22E)-(24R)-2-methylene-22-dehydro-1α,24,25-trihydroxy-19-nor-vitamin $D_3$ form and precipitate from the solution.

5. The method of claim 3, wherein the step of separating comprises filtering the mixture and precipitate to obtain the crystals.

6. The method of claim 3 including a further step (d) comprising repeating steps (a) through (c) using the recovered crystals of (22E)-(24R)-2-methylene-22-dehydro-1α,24,25-trihydroxy-19-nor-vitamin $D_3$ from step (c) in step (a).

7. The method of claim 3 wherein the mixture of ethyl acetate and hexane comprises about 20-30% ethyl acetate and about 70-80% hexane by volume.

8. A pharmaceutical composition containing an effective amount of the compound of claim 1 in crystalline form and a pharmaceutically acceptable excipient.

9. A method of treating or preventing a skin disease, disorder, or condition in a subject in need thereof, the method comprising administering to the subject an effective amount of the compound of claim 1 in crystalline form.

10. The method of claim 9, wherein the skin disease, disorder, or condition is psoriasis.

11. A method of treating or preventing a cell proliferative disease or disorder in a subject in need thereof, the method comprising administering to the subject an effective amount of the compound of claim 1 in crystalline form.

12. The method of claim 11, wherein the cell proliferative disease or disorder is selected from the group consisting of leukemia, neuroblastoma, retinoblastoma, melanoma, colon cancer, breast cancer, and prostate cancer.

13. A method of treating or preventing a disease or disorder in a subject in need thereof, the disease or disorder selected from the group consisting of multiple sclerosis, diabetes mellitus, lupus, host versus graft reaction, and rejection of transplants, the method comprising administering to the subject an effective amount of the compound of claim 1 in crystalline form.

14. A method of treating or preventing an inflammatory disease or disorder in a subject in need thereof, the method comprising administering to the subject an effective amount of the compound of claim 1 in crystalline form.

15. The method of claim 14, wherein the inflammatory disease or disorder is selected from the group consisting of rheumatoid arthritis, asthmas, and inflammatory bowel diseases.

16. The method of claim 14, wherein the inflammatory disease or disorder is selected from the group consisting of Crohn's disease and ulcerative colitis.

17. A method of treating or preventing obesity, inhibiting adipocyte differentiation, inhibiting SCD-1 gene transcription, and/or reducing body fat in a subject in need thereof, the method comprising administering to the subject an effective amount of the compound of claim 1 in crystalline form.

* * * * *